US012319710B2

(12) United States Patent
Jørgensen et al.

(10) Patent No.: US 12,319,710 B2
(45) Date of Patent: Jun. 3, 2025

(54) CATECHOLAMINE PRODRUGS FOR USE IN THE TREATMENT OF PARKINSON'S DISEASES

(71) Applicant: H. Lundbeck A/S, Valby (DK)

(72) Inventors: Morten Jørgensen, Valby (DK); Martin Juhl, Valby (DK); Klaus Gjervig Jensen, Valby (DK)

(73) Assignee: H. Lundbeck A/S, Valby (DK)

(*) Notice: Subject to any disclaimer, the term of this patent is extended or adjusted under 35 U.S.C. 154(b) by 824 days.

(21) Appl. No.: 17/606,313

(22) PCT Filed: May 19, 2020

(86) PCT No.: PCT/EP2020/063915
§ 371 (c)(1),
(2) Date: Oct. 25, 2021

(87) PCT Pub. No.: WO2020/234275
PCT Pub. Date: Nov. 26, 2020

(65) Prior Publication Data
US 2022/0213136 A1    Jul. 7, 2022

(30) Foreign Application Priority Data
May 21, 2019   (DK) .............................. PA201900610

(51) Int. Cl.
*C07H 15/26* (2006.01)
(52) U.S. Cl.
CPC .................................. *C07H 15/26* (2013.01)
(58) Field of Classification Search
None
See application file for complete search history.

(56) References Cited

U.S. PATENT DOCUMENTS

| | | | |
|---|---|---|---|
| 3,132,171 A | 5/1964 | Plaut | |
| 4,374,829 A | 2/1983 | Harris | |
| 4,543,256 A | 9/1985 | Neumeyer | |
| 4,565,818 A | 1/1986 | Nordmann et al. | |
| 4,692,453 A | 9/1987 | Seiler | |
| 5,073,547 A | 12/1991 | Casagrande et al. | |
| 5,747,513 A | 5/1998 | Montanari et al. | |
| 5,885,988 A | 3/1999 | Neumann et al. | |
| 5,955,468 A | 9/1999 | Markstein | |
| 8,129,530 B2 | 3/2012 | Jorgensen et al. | |
| 10,729,710 B2 | 8/2020 | Jensen et al. | |
| 11,104,697 B2 | 8/2021 | Juhl et al. | |
| 11,110,110 B2 | 9/2021 | Jensen et al. | |
| 11,111,263 B2 | 9/2021 | Juhl et al. | |
| 11,130,775 B2 | 9/2021 | Jensen et al. | |
| 11,168,056 B2 | 11/2021 | Jacobsen et al. | |
| 11,707,476 B2 | 7/2023 | Jensen et al. | |
| 11,827,665 B2 | 11/2023 | Juhl et al. | |
| 11,851,456 B2 | 12/2023 | Juhl et al. | |
| 11,858,954 B2 | 1/2024 | Jensen et al. | |
| 11,866,410 B2 | 1/2024 | Jacobsen et al. | |
| 2009/0062324 A1 | 3/2009 | Jorgensen et al. | |
| 2009/0124651 A1 | 5/2009 | Jorgensen et al. | |
| 2012/0077836 A1 | 3/2012 | Wilkstrom et al. | |
| 2017/0335357 A1 | 11/2017 | Divi et al. | |
| 2020/0338102 A1 | 1/2020 | Balmer et al. | |
| 2020/0369615 A1 | 11/2020 | Jacobsen et al. | |
| 2020/0369705 A1 | 11/2020 | Juhl et al. | |
| 2020/0369706 A1 | 11/2020 | Juhl et al. | |
| 2020/0392176 A1 | 12/2020 | Jensen et al. | |
| 2022/0024875 A1 | 1/2022 | Jacobsen et al. | |
| 2022/0024962 A1 | 1/2022 | Jensen et al. | |
| 2022/0185839 A1 | 6/2022 | Juhl et al. | |
| 2022/0194978 A1 | 6/2022 | Juhl et al. | |
| 2022/0213040 A1 | 7/2022 | Jorgensen et al. | |
| 2022/0213071 A1 | 7/2022 | Jorgensen et al. | |
| 2022/0220077 A1 | 7/2022 | Jorgensen et al. | |
| 2022/0257623 A1 | 8/2022 | Jensen et al. | |
| 2024/0018107 A1 | 1/2024 | Jacobsen et al. | |
| 2024/0025857 A1 | 1/2024 | Jørgensen et al. | |
| 2024/0156851 A1 | 5/2024 | Jensen et al. | |
| 2024/0190909 A1 | 6/2024 | Jensen et al. | |

(Continued)

FOREIGN PATENT DOCUMENTS

| | | |
|---|---|---|
| CN | 102746351 A | 10/2012 |
| CN | 105218606 A | 1/2016 |
| EP | 0 352 815 A1 | 1/1990 |

(Continued)

OTHER PUBLICATIONS

Fernández, C., Nieto, O., Rivas, E., Montenegro, G., Fontenla, J. A., & Fernández-Mayoralas, A. (2000). Synthesis and biological studies of glycosyl dopamine derivatives as potential antiparkinsonian agents. Carbohydrate research, 327(4), 353-365. (Year: 2000).*
International Search Report and Written Opinion for Application No. PCT/EP2020/063915 mailed Jul. 13, 2020.
U.S. Appl. No. 16/198,917, filed Nov. 23, 2018, Granted, U.S. Pat. No. 10,729,710.
U.S. Appl. No. 16/872,802, filed May 12, 2020, Granted, U.S. Pat. No. 11,110,110.
U.S. Appl. No. 17/386,686, filed Jul. 28, 2021, Pending.
U.S. Appl. No. 16/876,843, filed May 18, 2020, Granted, U.S. Pat. No. 11,104,697.
U.S. Appl. No. 17/385,166, filed Jul. 26, 2021, Pending.
U.S. Appl. No. 16/876,878, filed May 18, 2020, Granted, U.S. Pat. No. 11,111,263.

(Continued)

*Primary Examiner* — Dale R Miller
(74) *Attorney, Agent, or Firm* — Wolf, Greenfield & Sacks, P.C.

(57) ABSTRACT

The present invention provides compounds of formula (Id) that are prodrugs of catecholamine for use in treatment of neurodegenerative diseases and disorders. The present invention also provides pharmaceutical compositions comprising compounds of the invention and methods of treating neurodegenerative or neuropsychiatric diseases and disorders using the compounds of the invention, in particular Parkinson's disease.

29 Claims, 4 Drawing Sheets

(56) References Cited

U.S. PATENT DOCUMENTS

2024/0352055 A1 10/2024 Juhl et al.

FOREIGN PATENT DOCUMENTS

| | | |
|---|---|---|
| GB | 2 192 394 A | 1/1998 |
| JP | S60-172975 A | 9/1985 |
| JP | 2007-532670 A | 11/2007 |
| JP | 2010-536889 A | 12/2010 |
| WO | WO 90/12574 A1 | 11/1990 |
| WO | WO 97/03054 A1 | 1/1997 |
| WO | WO 98/38155 A1 | 9/1998 |
| WO | WO 00/47571 A1 | 8/2000 |
| WO | WO 01/36428 A1 | 5/2001 |
| WO | WO 01/76602 A1 | 10/2001 |
| WO | WO 01/78713 A1 | 10/2001 |
| WO | WO 02/13827 A1 | 2/2002 |
| WO | WO 02/14279 A1 | 2/2002 |
| WO | WO 02/100377 A1 | 12/2002 |
| WO | WO 03/006458 A1 | 1/2003 |
| WO | WO 03/013532 A1 | 2/2003 |
| WO | WO 03/074511 A1 | 9/2003 |
| WO | WO 03/080074 A1 | 10/2003 |
| WO | WO 2004/052841 A1 | 6/2004 |
| WO | WO 2005/062894 A2 | 7/2005 |
| WO | WO 2006/012640 A2 | 2/2006 |
| WO | WO 2006/056604 A1 | 6/2006 |
| WO | WO 2009/026934 A1 | 3/2009 |
| WO | WO 2009/026935 A1 | 3/2009 |
| WO | WO 2009/156458 A1 | 12/2009 |
| WO | WO 2010/097091 A1 | 9/2010 |
| WO | WO 2010/097092 A1 | 9/2010 |
| WO | WO 2013/020979 A1 | 2/2013 |
| WO | WO 2013/034119 A1 | 3/2013 |
| WO | WO 2015/067927 A1 | 5/2015 |
| WO | WO 2016/065019 A1 | 4/2016 |
| WO | WO 2017/184871 A1 | 10/2017 |
| WO | WO 2019/101917 A1 | 5/2019 |
| WO | WO 2020/234271 A1 | 11/2020 |

OTHER PUBLICATIONS

U.S. Appl. No. 17/391,439, filed Aug. 2, 2021, Pending.
U.S. Appl. No. 16/876,908, filed May 18, 2020, Granted, U.S. Pat. No. 11,130,775.
U.S. Appl. No. 17/392,970, filed Aug. 3, 2021, Published, 2022-0024962.
U.S. Appl. No. 16/876,966, filed May 18, 2020, Granted, U.S. Pat. No. 11,168,056.
U.S. Appl. No. 17/495,997, filed Oct. 7, 2021, Published, 2022-0024875.
U.S. Appl. No. 17/606,319, filed Oct. 25, 2021, Pending.
U.S. Appl. No. 17/606,332, filed Oct. 25, 2021, Pending.
U.S. Appl. No. 17/606,303, filed Oct. 25, 2021, Pending.
PCT/EP2020/063916, Sep. 28, 2020, International Search Report and Written Opinion.
PCT/EP2020/063918, Aug. 10, 2020, International Search Report and Written Opinion.
PCT/EP2020/063914, Jul. 14, 2020, International Search Report and Written Opinion.
PCT/EP2018/082361, Feb. 22, 2019, International Search Report and Written Opinion.
PCT/EP2020/063909, Jul. 2, 2020, International Search Report and Written Opinion.
PCT/EP2020/063910, Jul. 14, 2020, International Search Report and Written Opinion.
PCT/EP2020/063913, Jul. 15, 2020, International Search Report and Written Opinion.
PCT/EP2020/063908, Sep. 11, 2020, International Search Report and Written Opinion.
PCT/EP2020/063915, Jul. 13, 2020, International Search Report and Written Opinion.

International Search Report and Written Opinion for Application No. PCT/EP2020/063916 mailed Sep. 28, 2020.
International Search Report and Written Opinion for Application No. PCT/EP2020/063918 mailed Aug. 10, 2020.
International Search Report and Written Opinion for Application No. PCT/EP2020/063914 mailed Jul. 14, 2020.
International Search Report and Written Opinion for Application No. PCT/EP2018/082361 mailed Feb. 22, 2019.
International Search Report and Written Opinion for Application No. PCT/EP2020/063909 mailed Jul. 2, 2020.
International Search Report and Written Opinion for Application No. PCT/EP2020/063910 mailed Jul. 14, 2020.
International Search Report and Written Opinion for Application No. PCT/EP2020/063913 mailed Jul. 15, 2020.
International Search Report and Written Opinion for Application No. PCT/EP2020/063908 mailed Sep. 11, 2020.
Ahari et al., A direct stereoselective approach to trans-2,3-disubstituted piperidines: application in the synthesis of 2-Epi-CP-99,994 and (+)-epilupinine. Org Lett. Jun. 19, 2008;10(12):2473-6. doi: 10.1021/01800722a. Epub May 14, 2008.
Alexander et al., Functional architecture of basal ganglia circuits: neural substrates of parallel processing. Trends Neurosci. Jul. 1990;13(7):266-71.
Atkinson et al., Derivatives of apomorphine and of other N-substituted norapomorphines. J Pharm Sci. Nov. 1976;65(11):1682-5.
Bibbiani et al., Continuous dopaminergic stimulation reduces risk of motor complications in parkinsonian primates. Exp Neurol. Mar. 2005;192(1):73-8.
Billeter et al., 8-Hydroxyflavonoid Glucuronides from Malva Sylvestris. Phytochemistry. 1991; 30(3):987-90.
Brown et al., Structurally constrained hybrid derivatives containing octahydrobenzo[g or f]quinoline moieties for dopamine D2 and D3 receptors: binding characterization at D2/D3 receptors and elucidation of a pharmacophore model. J Med Chem. Dec. 25, 2008;51(24):7806-19. doi: 10.1021/jm8008629.
Campbell et al., Behavioral effects of (-)10,11-methylenedioxy-N-n-propylnoraporphine, an orally effective long-acting agent active at central dopamine receptors, and analogous aporphines. Neuropharmacology. Oct. 1982;21(10):953-61.
Cannon et al., N-Alkyl derivatives of trans-6,7-dihydroxy-1,2,3,4,4a,5,10,10b-octahyrobenzo[g]quinoline A congener of apomorphine lacking the non-oxygenated aromatic ring. J. Heterocyclic Chem. Nov. 1980;17:1633-1636.
Cavero et al., Safety Pharmacology assessment of drugs with biased 5-HT(2B) receptor agonism mediating cardiac valvulopathy. J Pharmacol Toxicol Methods. Mar.-Apr. 2014;69(2):150-61. doi: 10.1016/j.vascn.2013.12.004. Epub Dec. 19, 2013.
Delong, Primate models of movement disorders of basal ganglia origin. Trends Neurosci. Jul. 1990;13(7):281-5.
Di Stefano et al., Antiparkinson prodrugs. Molecules. Jan. 16, 2008;13(1):46-68.
Fan et al., Differential effects of pro-BDNF on sensory neurons after sciatic nerve transection in neonatal rats. Eur J Neurosci. May 2008;27(9):2380-90. doi: 10.1111/j.1460-9568.2008.06215.x. Epub Apr. 22, 2008.
Fan et al., Modifications of the isonipecotic acid fragment of SNS-032: analogs with improved permeability and lower efflux ratio. Bioorg Med Chem Lett. Dec. 1, 2008;18(23):6236-9. doi: 10.1016/j.bmcl.2008.09.099. Epub Oct. 2, 2008. (citation on PubMed).
Fumeaux et al., First synthesis, characterization, and evidence for the presence of hydroxycinnamic acid sulfate and glucuronide conjugates in human biological fluids as a result of coffee consumption. Org Biomol Chem. Nov. 21, 2010;8(22):5199-211. doi: 10.1039/c0ob00137f. Epub Sep. 14, 2010.
Gerfen et al., D1 and D2 dopamine receptor-regulated gene expression of striatonigral and striatopallidal neurons. Science. Dec. 7, 1990;250(4986):1429-32.
Giardina et al., Adrogolide HCI (ABT-431; DAS-431), a prodrug of the dopamine D1 receptor agonist, A-86929: preclinical pharmacology and clinical data. CNS Drug Rev. 2001 Fall;7(3):305-16.

(56) References Cited

OTHER PUBLICATIONS

Goswami et al., Intestinal absorption and metabolism of retinoyl beta-glucuronide in humans, and of 15-[14C]-retinoyl beta-glucuronide in rats of different vitamin A status. J Nutr Biochem. Dec. 2003;14(12):703-9.

Grosset et al., Inhaled dry powder apomorphine (VR040) for 'off' periods in Parkinson's disease: an in-clinic double-blind dose ranging study. Acta Neurol Scand. Sep. 2013;128(3):166-71. doi: 10.1111/ane.12107. Epub Mar. 26, 2013.

Hauser et al., Sublingual apomorphine (APL-130277) for the acute conversion of OFF to ON in Parkinson's disease. Mov Disord. Sep. 2016;31(9):1366-72. Epub Jul. 19, 2016.

Knobloch et al., Keto Esters Derived from 2-(Trimethylsilyl) ethanol: An Orthogonal Protective Group for β-Keto Esters. Synthesis 2008.14 (2008): 2229-2246.

Kotsuki et al., Highly practical, enantiospecific synthesis of the cyclohexyl fragment of the immunosuppressant FK-506. J Org Chem. Aug. 1992;57(18):5036-40.

Liu et al., A novel synthesis and pharmacological evaluation of a potential dopamine D1/D2 agonist: 1-propyl-1,2,3,4,4a,5,10,10a-octahydrobenzo[g]quinoline-6,7-diol. Bioorg Med Chem. Mar. 15, 2008;16(6):3438-44. doi: 10.1016/j.bmc.2007.06.036. Epub Jun. 23, 2007.

Liu et al., Extremely potent orally active benzo[g]quinoline analogue of the dopaminergic prodrug: 1-propyl-trans-2,3,4,4a,5,7,8,9,10,10a-decahydro-1H-benzo-[g]quinolin-6-one [corrected]. J Med Chem. Feb. 23, 2006;49(4):1494-8. Erratum in: J Med Chem. Nov. 16, 2006;49(23):6930.

Loozen et al., An approach to the synthesis of [2] benzopyrano [3, 4?c] pyrroles; alternative dopaminergic molecules. Recueil des Travaux Chimiques des Pays?Bas. 1982;101(9):298-310.

Morissette et al., High-throughput crystallization: polymorphs, salts, co-crystals and solvates of pharmaceutical solids. Adv Drug Deliv Rev. Feb. 23, 2004;56(3):275-300. doi: 10.1016/j.addr.2003.10.020.

Nolen et al., Budesonide-beta-D-glucuronide: a potential prodrug for treatment of ulcerative colitis. J Pharm Sci. Jun. 1995;84(6):677-81.

Poewe et al., Parkinson disease. Nat Rev Dis Primers. Mar. 23, 2017;3:17013.

Rothman et al., Evidence for possible involvement of 5-HT(2B) receptors in the cardiac valvulopathy associated with fenfluramine and other serotonergic medications. Circulation. Dec. 5, 2000;102(23):2836-41.

Sozio et al., Designing prodrugs for the treatment of Parkinson's disease. Expert Opin Drug Discov. May 2012;7(5):385-406. Epub Apr. 12, 2012.

Sprenger et al., Management of motor and non-motor symptoms in Parkinson's disease. CNS Drugs. Apr. 2013;27(4):259-72.

Stain-Texier et al., Intestinal absorption and stability of morphine 6-glucuronide in different physiological compartments of the rat. Drug Metab Dispos. May 1998;26(5):383-7.

Zhang et al., Flavonoid metabolism: the synthesis of phenolic glucuronides and sulfates as candidate metabolites for bioactivity studies of dietary flavonoids. Tetrahedron. 2012; 68:4194-4201.

Banker et al., Modern Pharmaceuticals. Third Edition, Revised and Expanded. Marcel Dekker, Inc., New York, 1996. p. 596.

David et al., Control of catalytic debenzylation and dehalogenation reactions during liquid-phase reduction by H2. Journal of Catalysis. 2006; 237(2): 349-358.

Kummerer, K. Pharmaceuticals in the Environment. Annu. Rev. Environ. Resour. 2010. 35:57-75. doi: 10.1146/annurev-environ-052809-161223.

Levin et al., Cognitive and neuropsychiatric disorders in extrapyramidal diseases. Neurology, Neuropsychiatry, Psychosomatics. 2012;4(2S):22-30. https://doi.org/10.14412/2074-2711-2012-2505.

Mironov, The Guidelines for Preclinical Trials of Medicinal Products. Grif & Co. Moscow, Russia. 2012. 941 pages.

Przedborski et al., Neurodegeneration: What is it and where are we? J Clin Invest. 2003;111(1):3-10. https://doi.org/10.1172/JCI17522.

Sun et al., Oral bioavailability and brain penetration of (−)-stepholidine, a tetrahydroprotoberberine agonist at dopamine D(1) and antagonist at D(2) receptors, in rats. Br J Pharmacol. Nov. 2009;158(5):1302-12. Epub Sep. 25, 2009.

Szajewska, H. Evidence-based medicine and clinical research: both are needed, neither is perfect. Ann Nutr Metab. 2018;72 Suppl 3:13-23. doi: 10.1159/000487375. Epub Apr. 9, 2018. PMID: 29631266.

Ugrumov M.V., Development of preclinical diagnosis and preventive treatment of neurodegenerative diseases. Zh Nevrol Psikhiatr Im S S Korsakova. 2015;115(11):4-14. Russian. doi: 10.17116/jnevro20151151114-14.

Wesserling et al., Will in vitro tests replace animal models in experimental oncology? J Tissue Scie Eng. 2011; 2:102e. doi: 10.4172/2157-7552.1000102e.

Wolff, M.E. Burger's Medicinal Chemistry and Drug Discovery. Volume 1, Principles and Practice, Fifth Edition. John Wiley & Sons 1995. pp. 975-977.

Byrn et al., Pharmaceutical Solids: A Strategic Approach to Regulatory Considerations. Pharmaceutical Research. 1995;12(7):945-54.

Caira, Crystalline Polymorphism of Organic Compounds. Design of Organic Solids. Topics in Current Chemistry.1998(198):163-208.

Choi et al., Dopamine Agonists. NIH National Library of Medicine, In: StatPearls [Internet].Treasure Island (FL): StatPearls Publishing;. Jan. 2024. Last updated Jun. 26, 2023, 8 pages.

Clarke, Recent developments in the homogeneous hydrogenation of carboxylic acid esters. Catal. Sci. Technol. Sep. 25, 2012;2:2418-23.

Elger et al., Estrogen sulfamates: a new approach to oral estrogen therapy. Reprod Fertil Dev. 2001;13(4):297-305. doi: 10.1071/rd01029.

Elger et al., Novel oestrogen sulfamates: a new approach to oral hormone therapy. Expert Opin Investig Drugs. Apr. 1998;7(4):575-89. doi: 10.1517/13543784.7.4.575.

Elger et al., Sulfamates of various estrogens are prodrugs with increased systemic and reduced hepatic estrogenicity at oral application. J Steroid Biochem Mol Biol. Dec. 1995;55(3-4):395-403. doi: 10.1016/0960-0760(95)00214-6.

Kuznetsova, Qualitative X-ray phase analysis—Methodological guidelines. Irkutsk State University, General Physics Department. 2005;6 pages.

Malmquist et al., The synthesis of tritiated (R)-2-methoxy-N-n-propyl-nor-apomorphine (MNPA). J Label Compd Radiopharm. Sep. 2007;50(13):1211-1214.

Reutov et al., Organic Chemistry: Manual for Chemical Students and Post-Graduates. 1999; 903-904; 905; 1738-1739 (with reference to N. Kornblum, 1963).

Reutov et al., Organic Chemistry: textbook for students of chemical specialties and graduate students.1999. Chapter 27, Section 27.9.1. c., 1999;6 pages.

Yu, Amorphous pharmaceutical solids: preparation, characterization and stabilization. Adv Drug Deliv Rev. May 1, 20016;48(1):27-42. doi: 10.1016/s0169-409x(01)00098-9.

Yujian et al., Prodrug: Design and Clinical Application. Int J Pharm Res. Oct. 2008;5(35): 377-380, 387.

\* cited by examiner

CATECHOLAMINE PRODRUGS FOR USE IN THE TREATMENT OF PARKINSON'S DISEASES

CROSS REFERENCE TO RELATED APPLICATIONS

This Application is a National Stage filing under 35 U.S.C. 371 of International PCT Application No. PCT/EP2020/063915, filed May 19, 2020, which claims priority to Denmark Application Number PA201900610, filed May 21, 2019. The entire contents of these applications are incorporated herein by reference in their entirety.

FIELD OF THE INVENTION

The present invention provides compounds that are prodrugs of the dopamine agonist (4aR,10aR)-1-Propyl-1,2,3,4,4a,5,10,10a-octahydro-benzo[g]quinoline-6,7-diol and their use in the treatment of Parkinson's disease and/or other conditions for which treatment with a dopamine agonist is therapeutically beneficial such as but not limited to Restless leg syndrome, Huntington's disease and Alzheimer's disease; and also neuropsychiatric diseases and disorders such as but not limited to schizophrenia, attention deficit hyperactivity disorder and drug addiction. The present invention also provides pharmaceutical compositions comprising compounds of the invention.

BACKGROUND OF THE INVENTION

Parkinson's disease (PD) is a common neurodegenerative disorder that becomes increasingly prevalent with age and affects an estimated seven to ten million people worldwide. Parkinson's disease is a multi-faceted disease characterized by both motor and non-motor symptoms. Motor symptoms include resting tremor (shaking), bradykinesia/akinesia (slowness and poverty of movements), muscular rigidity, postural instability and gait dysfunction; whereas non-motor symptoms include neuropsychiatric disorders (e.g. depression, psychotic symptoms, anxiety, apathy, mild-cognitive impairment and dementia) as well as autonomic dysfunctions and sleep disturbances (Poewe et al., Nature Review, (2017) vol 3 article 17013: 1-21).

A key hallmark of Parkinson's disease pathophysiology is the loss of pigmented dopaminergic neurons in the substantia nigra pars compacta that provides dopaminergic innervation to the striatum and other brain areas. Such progressive neurodegeneration leads to the decrease in dopamine striatal levels which ultimately results in a series of changes in the basal ganglia circuitry, ultimately ending up in the occurrence of the four cardinal motor features of Parkinson's disease. The main target of dopamine in the striatum consists of medium spiny GABAergic neurons (MSNs) selectively expressing D1 or D2 receptors pending topographical projections. GABAergic-MSN projecting to the external pallidum, also called striato-pallidal 'indirect pathway' express D2 receptors (MSN-2); whereas GABAergic-MSN projecting to the substantia nigra pars reticulata and internal pallidum, also called striato-nigral 'direct pathway' express D1 receptors (MSN-1). Depletion of dopamine because of neuronal loss results in an imbalanced activity of the two pathways, resulting in a marked reduction of thalamic and cortical output activities and ultimately motor dysfunctions (Gerfen et al, Science (1990) 250: 1429-32; Delong, (1990) Trends in Neuroscience 13: 281-5; Alexander et Crutcher, (1990) Trends in Neuroscience 13: 266-71; and for review Poewe et al., Nature Review (2017) vol. 3 article 17013: 1-21).

The most effective therapeutic strategies available to patients suffering from Parkinson's disease, and aiming at controlling motor symptoms are primarily indirect and direct dopamine agonists. The classic and gold standard treatment regimen includes chronic oral intake of L-3,4-dihydroxy phenylalanine (L-DOPA) which is decarboxylated in the brain to form dopamine. Other approaches consist in the administration of dopamine receptor agonists such as apomorphine which acts both on the D1 and D2 receptors subtypes, or pramipexole, ropinirole and others which are predominantly directed towards D2 receptors subtypes. Optimal motor relief is obtained with use of both L-DOPA and apomorphine due to their activation of both D1 and D2 receptor subtypes and holistic re-equilibrium of the indirect-direct pathways (i.e. while D2 agonists only reverse the indirect pathway dysfunction).

L-DOPA and apomorphine with the structures depicted below are currently the most efficacious PD drugs in clinical use.

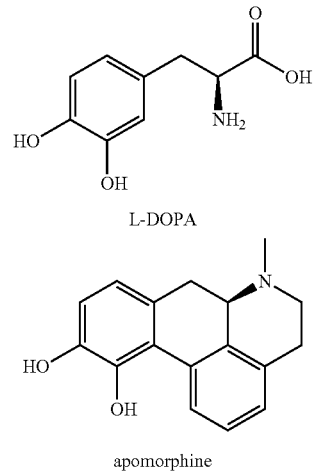

L-DOPA apomorphine

L-DOPA is a prodrug of dopamine and remains the most efficacious drug in the treatment of motor Parkinson's disease. However, after several years of treatment (i.e. honeymoon period), complications arise due the inherent progression of the disease (i.e. sustained loss of dopaminergic neurons) as well as poor pharmacokinetic (PK) profile of L-DOPA. Those complications include: 1) dyskinesia which are abnormal involuntary movements occurring during the optimal 'on-time effect' of the drug; and 2) off fluctuations, period during which the L-DOPA positive effect wears off and symptoms re-emerge or worsen (Sprenger and Poewe, CNS Drugs (2013), 27: 259-272).

Direct dopamine receptor agonists are able to activate the dopamine autoreceptors as well as the postsynaptic dopamine receptors located on the medium spiny neurons MSN-1 and MSN-2. Apomorphine belongs to a class of dopamine agonists with a 1,2-dihydroxybenzene (catechol) moiety. When combined with a phenethylamine motif, catecholamines often possess low or no oral bioavailability as is the case for apomorphine. Apomorphine is used clinically in PD therapy albeit with a non-oral delivery (typically intermittent subcutaneous administration or daytime continuous parenteral infusion via a pump). For apomorphine, animal studies have shown that transdermal delivery or implants may provide possible forms of administration. However, when the delivery of apomorphine from implants was studied in monkeys (Bibbiani et al., Chase Experimental Neurology (2005), 192: 73-78) it was found that in most cases the animals had to be treated with the immunosuppressant dexamethasone to prevent local irritation and other complications following the implantation surgery. Alternative delivery strategies for apomorphine therapy in PD such as inhalation and sublingual formulations have been extensively explored (see e.g. Grosset et al., Acta Neurol Scand. (2013), 128:166-171 and Hauser et al., Movement Disorders (2016), Vol. 32 (9): 1367-1372). However, these efforts are yet not in clinical use for the treatment of PD.

An alternative to the non-oral formulations of the catecholamines involves the use of a prodrug masking the free catechol hydroxyl groups to enable oral administration. However, a known problem associated with the development of prodrugs for clinical use is the difficulties associated with predicting conversion to the parent compound in humans.

Various ester prodrugs of catecholamines have been reported in the literature such as enterically coated N-propyl-apomorphine (NPA) esters for duodenal delivery (see eg. WO 02/100377), and the D1-like agonist adrogolide, a diacetyl prodrug of A-86929 (Giardina and Williams; CNS Drug Reviews (2001), Vol. 7 (3): 305-316). Adrogolide undergoes extensive hepatic first-pass metabolism in man after oral dosing and, as a result, has a low oral bioavailability (app. 4%). In PD patients, intravenous (IV) adrogolide has antiparkinson efficacy comparable to that of L-DOPA (Giardina and Williams; CNS Drug Reviews (2001), Vol. 7 (3): 305-316).

In addition to the ester prodrugs of catecholamines, an alternative prodrug approach involves the masking of the two catechol hydroxyl groups as the corresponding methylene-di-oxy (MDO) acetal, as the acetal derived from other aldehydes than formaldehyde, or as the ketal derived from various ketones. This prodrug principle has been described for example in Campbell et al., Neuropharmacology (1982); 21(10): 953-961 and in U.S. Pat. No. 4,543,256, WO 2009/026934 and WO 2009/026935.

Yet another suggested approach for a catecholamine prodrug is the formation of an enone derivative as suggested in for example WO 2001/078713 and in Liu et al., Bioorganic Med. Chem. (2008), 16: 3438-3444. For further examples of catecholamine prodrugs see for example Sozio et al., Exp. Opin. Drug Disc. (2012); 7(5): 385-406.

The compound (4aR,10aR)-1-Propyl-1,2,3,4,4a,5,10,10a-octahydro-benzo[g]quinoline-6,7-diol depicted as compound (I) below is disclosed in WO 2009/026934. The trans-isomer was disclosed previously in Liu eat al., J. Med. Chem. (2006), 49: 1494-1498 and then in Liu et al., Bioorganic Med. Chem. (2008), 16: 3438-3444 including pharmacological data indicating that the compound has a low oral bioavailability in rats. The racemate was disclosed for the first time in Cannon et al., J. Heterocyclic Chem. (1980); 17: 1633-1636.

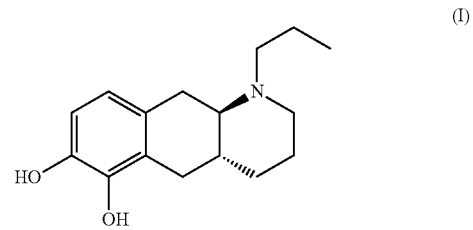 [SMILES: CCCN1CCC[C@@H]2Cc3c(ccc(O)c3O)C[C@H]21]

Compound (I) is a dopamine receptor agonist with mixed D1 and D2 activity. Three prodrug derivatives of compound (I) are known in the art.

Liu et al., J. Med. Chem. (2006), 49: 1494-1498 and Liu et al., Bioorganic Med. Chem. (2008), 16: 3438-3444 disclose the enone derivative of formula (Ia) depicted below which was shown to be converted to the active compound (I) in rats.

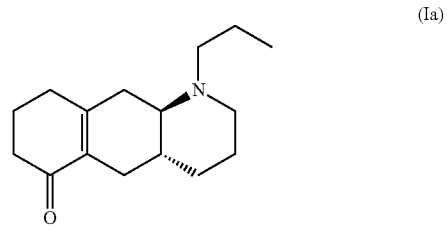 [SMILES: CCCN1CCC[C@@H]2CC3=C(CCCC3=O)C[C@H]21]

WO 2009/026934 and WO 2009/026935 disclose two types of prodrug derivatives of compound (I) including (6aR,10aR)-7-propyl-6,6a,7,8,9,10,10a,11-octahydro-[1,3]dioxolo[4',5':5,6]benzo[1,2-g]quinoline, a methylenedioxy (MDO) derivative with the formula (Ib) below:

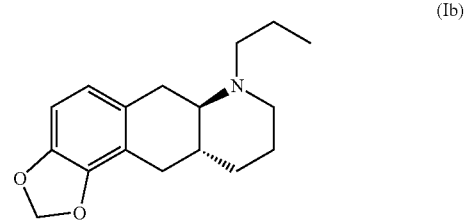 [SMILES: CCCN1CCC[C@@H]2Cc3c(ccc4c3OCO4)C[C@H]21]

The conversion of compound (Ib) to compound (I) in rat and human hepatocytes has been demonstrated in WO 2010/097092. Furthermore, the in vivo pharmacology of the compounds (Ia) and (Ib) as well as the active "parent compound" (I) has been tested in various animal models relevant for Parkinson's Disease (WO 2010/097092). Both compound (I) and compounds (Ia) and (Ib) were found to be effective, indicating that compounds (Ia) and (Ib) are converted in vivo to compound (I). All three compounds were reported to have a duration of action that was longer than observed for L-dopa and apomorphine.

The other prodrug of compound (I) disclosed in WO 2009/026934 and WO 2009/026935 is a conventional ester prodrug of the formula (Ic):

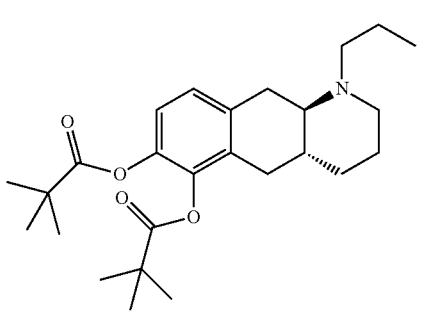
(Ic)

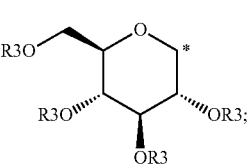
(i)

and wherein R3 is selected from H and —C(O)C$_1$-C$_6$ alkyl; and wherein * indicates the attachment point; and wherein the carbon atom at the attachment point on substituent (i) is in the S-configuration;

with the proviso that when one of R1 or R2 is substituent (i) and R3 is H then the other of R1 or R2 cannot be linear-C(O)C$_1$-C$_6$ alkyl;

or a pharmaceutically acceptable salt thereof.

One aspect of the invention relates to a pharmaceutical composition comprising a compound according formula (Id) or a pharmaceutically acceptable salt thereof, and one or more pharmaceutically acceptable excipients.

Another aspect of the invention relates to a compound according to formula (Id) for use as a medicament.

Another aspect of the invention relates to a compound according to formula (Id) or a pharmaceutically acceptable salt thereof for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

Another aspect of the invention relates to a method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound of formula (Id) or a pharmaceutically acceptable salt thereof, to a patient in need thereof.

Another aspect of the invention relates to the use of a compound according to formula (Id) or a pharmaceutically acceptable salt thereof, for the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

Despite the long-standing interest in the field, there is evidently still an unmet need as regards developing efficient, well-tolerated and orally active drugs for the treatment of PD. A prodrug derivative of a mixed D1/D2 agonist giving a stable PK profile which can provide continuous dopaminergic stimulation may fulfil such unmet needs.

Levodopa glycosyl derivatives for treatment of Parkinson's Disease has been suggested in WO 2006/056604 supported by an in vitro experiment indicating intestinal transport. However, oral bioavailability in vivo has not been demonstrated. Glycoside derivatives of apomorphine has been disclosed in WO 03/080074 but conversion to apomorphine was not demonstrated.

Masking of catechol hydroxy groups of carbidopa derivatives with benzyl or small alkyl for improvement of intestinal absorption has been suggested in WO 2004/052841 but prodrug potential of such compounds was not demonstrated.

SUMMARY OF THE INVENTION

The present invention relates to new compounds for treatment of Parkinson's Disease. More particularly, the invention relates to new glycosyl derivatives, ester derivatives and ether derivatives of compound (I), which are prodrug derivatives of the compound (4aR,10aR)-1-Propyl-1,2,3,4,4a,5,10,10a-octahydro-benzo[g]quinoline-6,7-diol (compound (I)). The compounds of the invention have proven particularly useful for oral delivery of compound (I).

Accordingly, the present invention relates to compounds of formula (Id)

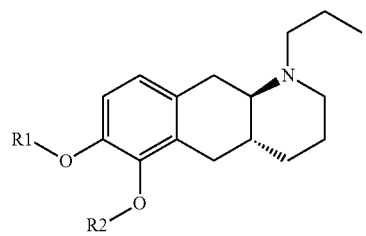
(Id)

wherein R1 and R2 are according to a)-c) below:

a) R1 is selected from H, C$_1$-C$_6$ alkyl, benzyl and linear —C(O)C$_1$-C$_6$ alkyl and R2 is substituent (i) below; or b) R1 is substituent (i) below and R2 is selected from H, C$_1$-C$_6$ alkyl, benzyl and linear —C(O)C$_1$-C$_6$ alkyl; or c) R1 and R2 are both represented by substituent (i) below Definitions Attachment Point In the context of the present invention, it is understood that the carbon atom at the attachment point on substituent (i) is at the anomeric position of (i).

Compounds of the Invention

Reference to compounds encompassed by the invention includes the free substance (e.g. free base or zwitter ion) of compounds of the invention, pharmaceutically acceptable salts of compounds of the invention, such as acid addition salts or base addition salts, and polymorphic and amorphic forms of compounds of the invention and of pharmaceutically acceptable salts thereof. Furthermore, the compounds of the invention and pharmaceutically acceptable salts thereof may potentially exist in unsolvated as well as in solvated forms with pharmaceutically acceptable solvents such as water, ethanol and the like. Both solvated and unsolvated forms are encompassed by the present invention.

Pharmaceutically Acceptable Salts

Pharmaceutically acceptable salts in the present context is intended to indicate non-toxic, i.e. physiologically acceptable salts.

The term "pharmaceutically acceptable salts" include pharmaceutically acceptable acid addition salts which are salts formed with inorganic and/or organic acids on the nitrogen atom in the parent molecule. Said acids may be selected from for example hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, malonic acid, fumaric acid, glutamic acid, pyroglutamic acid, salicylic acid, gentisic acid, saccharin, and sulfonic acids such as methanesulfonic acid, ethanesulfonic acid, toluenesulfonic acid, naphthalene-2-sulphonic acid, 2-hydroxy ethanesulphonic acid and benzenesulfonic acid.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Prodrug

In the present context, the terms "prodrug" or "prodrug derivative" indicates a compound that, after administration to a living subject, such as a mammal, preferably a human; is converted within the body into a pharmacologically active moiety. The conversion preferably takes place within a mammal, such as in a mouse, rat, dog, minipig, rabbit, monkey and/or human. In the present context a "prodrug of the compound (4aR,10aR)-1-Propyl-1,2,3,4,4a,5,10,10a-octahydro-benzo[g]quinoline-6,7-diol" or "a prodrug of the compound of formula (I)" or "a prodrug of compound (I)" is understood to be a compound that, after administration, is converted within the body into the compound (4aR,10aR)-Propyl-1,2,3,4,4a,5,10,10a-octahydro-benzo[g]quinoline-6,7-diol. Said administration may be by any conventional route of administration of pharmaceutical compositions known in the art, preferably by oral administration.

In the present context, the terms "parent compound" and "parent molecule" indicate the pharmacologically active moiety obtained upon conversion of a corresponding prodrug. For example, the "parent compound" of one of the compounds (Ia), (Ib), (Ic) or any of the compounds of the invention is understood to be the compound of formula (I).

Substituents

In the present context, a given range may interchangeably be indicated with "-" (dash) or "to", e.g. the term "$C_1$-$C_6$ alkyl" is equivalent to "$C_1$ to $C_6$ alkyl".

The term "alkyl" refers to a linear (i.e. unbranched) or branched saturated hydrocarbon, unless explicitly state otherwise, having from one up to ten carbon atoms, inclusive. Likewise, the term "$C_1$-$C_6$-alkyl" means a straight or branched chain hydrocarbon, unless explicitly state otherwise, containing from 1 to 6 carbon atoms. Examples of such groups include, but are not limited to, methyl, ethyl, 1-propyl, 2-propyl, 1-butyl, 2-butyl, 2-methyl-2-propyl, 2-methyl-1-butyl and n-hexyl. The term "linear $C_1$-$C_6$ alkyl" refers to a linear (i.e. unbranched) saturated hydrocarbon having from one up to six carbon atoms, inclusive. Examples of such groups include, methyl, ethyl, 1-propyl, 1-butyl, n-pentyl and n-hexyl.

The term "carbonyl" represents a —C(O)— group.

The term "alkylcarbonyl"" refers to an alkyl group as defined herein attached to the parent molecular moiety through a carbonyl group. Likewise, the term "—C(O)$C_1$-$C_6$-alkyl" refers to an $C_1$-$C_6$-alkyl as defined herein attached to the parent molecular moiety through a carbonyl group.

Pharmacokinetic Definitions and Abbreviations

As used herein, a "PK profile" is an abbreviation of "pharmacokinetic profile". Pharmacokinetic profiles and pharmacokinetic parameters described herein are based on the plasma concentration-time data obtained for the compound of formula (I) after oral dosing of a compound of the invention, using non-compartmental modelling. Abbreviated PK parameters are: $C_{max}$ (maximum concentration); $t_{max}$ (time to $C_{max}$); $t_{1/2}$ (half-life); $AUC_{0-24}$ (area under the curve from time of dosing and until 24 hours after dosing), and "Exposure at 24 h" is the plasma concentration of the compound of formula (I) as measured 24 hours after dosing.

Therapeutically Effective Amount

In the present context, the term "therapeutically effective amount" of a compound means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend e.g. on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the context of the present invention, a "therapeutically effective amount" of a compound of the invention indicates an amount of said compound of the invention that is able to provide an amount of compound (I) that is sufficient to alleviate, arrest, partly arrest, remove or delay the clinical manifestations of a given disease and its complications when said compound of the invention is administered, preferably by the oral route, to a mammal, preferably a human.

Treatment and Treating

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Conditions for Treatment

The compounds of the present invention are intended for treatment of neurodegenerative diseases and disorders such as Parkinson's disease and/or other conditions for which treatment with a dopamine agonist is therapeutically beneficial.

Therapeutic indications include a variety of central nervous system disorders characterized by motor and/or non-motor disturbances and for which part of the underlying pathophysiology is a dysfunction of the striatal-mediated circuitry. Such functional disturbances can be seen in neurodegenerative diseases such as but not limited to Parkinson's disease (PD), Restless leg syndrome, Huntington's disease, and Alzheimer's disease but also neuropsychiatric diseases such as, but not limited to, schizophrenia, attention deficit hyperactivity disorder and drug addiction.

In addition to neurodegenerative diseases and disorders, other conditions in which an increase in dopaminergic turnover may be beneficial are in the improvement of mental functions including various aspects of cognition. It may also have a positive effect in depressed patients, and it may also be used in the treatment of obesity as an anorectic agent and in the treatment of drug addiction. It may improve minimal brain dysfunction (MBD), narcolepsy, attention deficit hyperactivity disorder and potentially the negative, the positive as well as the cognitive symptoms of schizophrenia.

Restless leg syndrome (RLS) and periodic limb movement disorder (PLMD) are alternative indications, which are clinically treated with dopamine agonists. In addition, impotence, erectile dysfunction, SSRI induced sexual dysfunction, ovarian hyperstimulation syndrome (OHSS) and certain pituitary tumors (prolactinoma) are also likely to be improved by treatment with dopamine agonists. Dopamine is involved in regulation of the cardiovascular and renal systems, and accordingly, renal failure and hypertension can be considered alternative indications for the compounds of the invention.

The invention encompasses use of the compounds of the invention for treatment of the diseases and disorders listed above.

Combinations

In one embodiment of the invention, the compounds of formula (Id) are for use as stand-alone treatment as the sole active compound. In another embodiment of the invention, the compounds of formula (Id) may be used in combination with other agents useful in the treatment of a neurodegenerative disease or disorder such as Parkinson's disease. The terms "combined use", "in combination with" and "a combination of" and the like as used herein in the context of the method of the invention comprising the combined administration of therapeutically effective amounts of a compound of formula (Id), and another compound, which compound is useful in the treatment a neurodegenerative disease or disorder, is intended to mean the administration of a compound of formula (Id) simultaneously or sequentially, in any order, together with said other compound.

The two compounds may be administered simultaneously or with a time gap between the administrations of the two compounds. The two compounds may be administered either as part of the same pharmaceutical formulation or composition, or in separate pharmaceutical formulations or compositions. The two compounds may be administered on the same day or on different days. They may be administered by the same route, such for example by oral administration, subcutaneous injection, by transdermal administration, by depot, by intramuscular injection or intravenous injection; or by different routes wherein one compound is for example administered orally or placed by depot and the other compound is for example injected. The two compounds may be administered by the same dosage regime or interval, such as once or twice daily, weekly, or monthly; or by different dosage regimes for example wherein one is administered once daily and the other is administered twice daily or weekly or monthly.

In some instances, the patient to be treated may already be in treatment with one or more other compounds useful in the treatment of a neurodegenerative disease or disorder when treatment with a compound of formula (Id) is initiated. In other instances, the patient may already be in treatment with a compound of formula (Id) when treatment with one or more other compounds useful in the treatment of a neurodegenerative disease or disorder is initiated. In other instances, the treatment with a compound of formula (Id) and treatment with one or more other compounds useful in the treatment of a neurodegenerative disease or disorder is initiated at the same time.

Compounds for Combination Treatment

In the context of the invention, compounds to be used in combination with a compound of formula (Id) may be selected from for example L-DOPA, droxidopa, foliglurax, MAO-B inhibitors such as selegiline or rasagiline, COMT inhibitors such as entacapone or tolcapone, adenosine 2a antagonists such as istradefylline, antiglutamatergic agents such as amantadine or memantine, acetylcholinesterase inhibitors such as rivastigmine, donepezil or galantamine and antipsychotic agents such as quetiapine, clozapine, risperidone, pimavanserin, olanzapine, haloperidol, aripiprazole or brexpiprazole.

In addition to small molecules, compounds for combination could also include emerging biologics approaches in treatments for neurodegenerative diseases or disorders such as for example antibodies targeting alpha-synuclein, Tau or A-beta proteins.

Administration Routes

The pharmaceutical compositions comprising a compound of formula (Id), either as the sole active compound or in combination with another active compound, may be specifically formulated for administration by any suitable route such as the oral, rectal, nasal, buccal, sublingual, pulmonal, transdermal and parenteral (e.g. subcutaneous, intramuscular, and intravenous) route. In the context of the present invention the oral route is the preferred route of administration.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, carriers, fillers, diluents, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula (Id), such as one of the compounds disclosed in the Experimental Section herein. The present invention also provides a process for making a pharmaceutical composition comprising a compound of formula (Id). The pharmaceutical compositions according to the invention may be formulated with pharmaceutically acceptable excipients in accordance with conventional techniques such as those disclosed in Remington, "The Science and Practice of Pharmacy", $22^{th}$ edition (2013), Edited by Allen, Loyd V., Jr.

The pharmaceutical composition comprising a compound of the present invention is preferably a pharmaceutical composition for oral administration. Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses

In one embodiment, the compound of the present invention is administered in an amount from about 0.0001 mg/kg body weight to about 5 mg/kg body weight per day. In particular, daily dosages may be in the range of 0.001 mg/kg body weight to about 2 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.01-100 mg/day of a compound of the present invention, such as 0.05-50 mg/day, such as 0.1-10 mg/day or 0.1-5 mg/day. Conveniently, the compounds of the invention are administered in a unit dosage form containing said compounds in an amount of about 0.01 to 50 mg, such as 0.05 mg, 0.1 mg, 0.2 mg, 0.5 mg, 1 mg, 5 mg, 10 mg, 15 mg, 20 mg or up to 50 mg of a compound of the present invention.

DETAILED DESCRIPTION OF THE INVENTION

The inventors have identified new compounds that are prodrugs of (4aR,10aR)-1-Propyl-1,2,3,4,4a,5,10,10a-octahydro-benzo[g]quinoline-6,7-diol [compound (I)] which is a dual D1/D2 agonist (see for example WO 2009/026934).

The compounds are glycosyl derivatives, ester derivatives and ether derivatives of compound (I).

It was found that oral dosing of representative compounds of the invention in Wistar rats provides a systemic exposure of compound (I) in plasma, suggesting the usefulness of said compounds as orally active prodrugs of compound (I).

For all the compounds, the doses were corrected by molecular weight to equal a dose of 300 ag/kg of compound (Ib) corresponding to 287 ag/kg of compound (I).

Figure 2A:
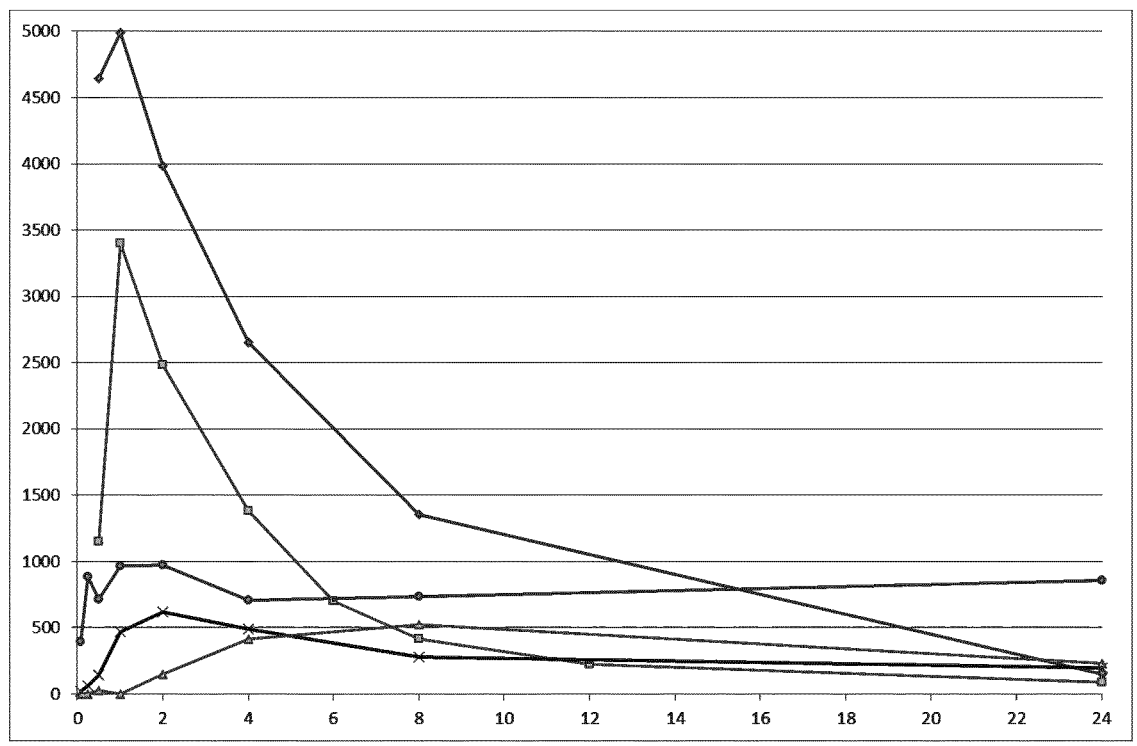
FIG. 2: PK profiles in Wistar rats obtained after oral dosing according to Example 3. Profiles are based on mean plasma concentrations from 3 subjects for each compound.
X-axis: time (hours); Y-axis: plasma concentration of Compound (I) (pg/mL)
2a: profiles obtained after dosing of the following compounds ■: compound (Ia); ♦: compound (Ib); ●: compound (4); X: Compound (7) and ▲: Compound (9).
2b: profiles obtained after dosing of the following compounds ■: compound (Ia), ♦: compound (Ib), ▲: A6, □: A2.
Figure 2B:
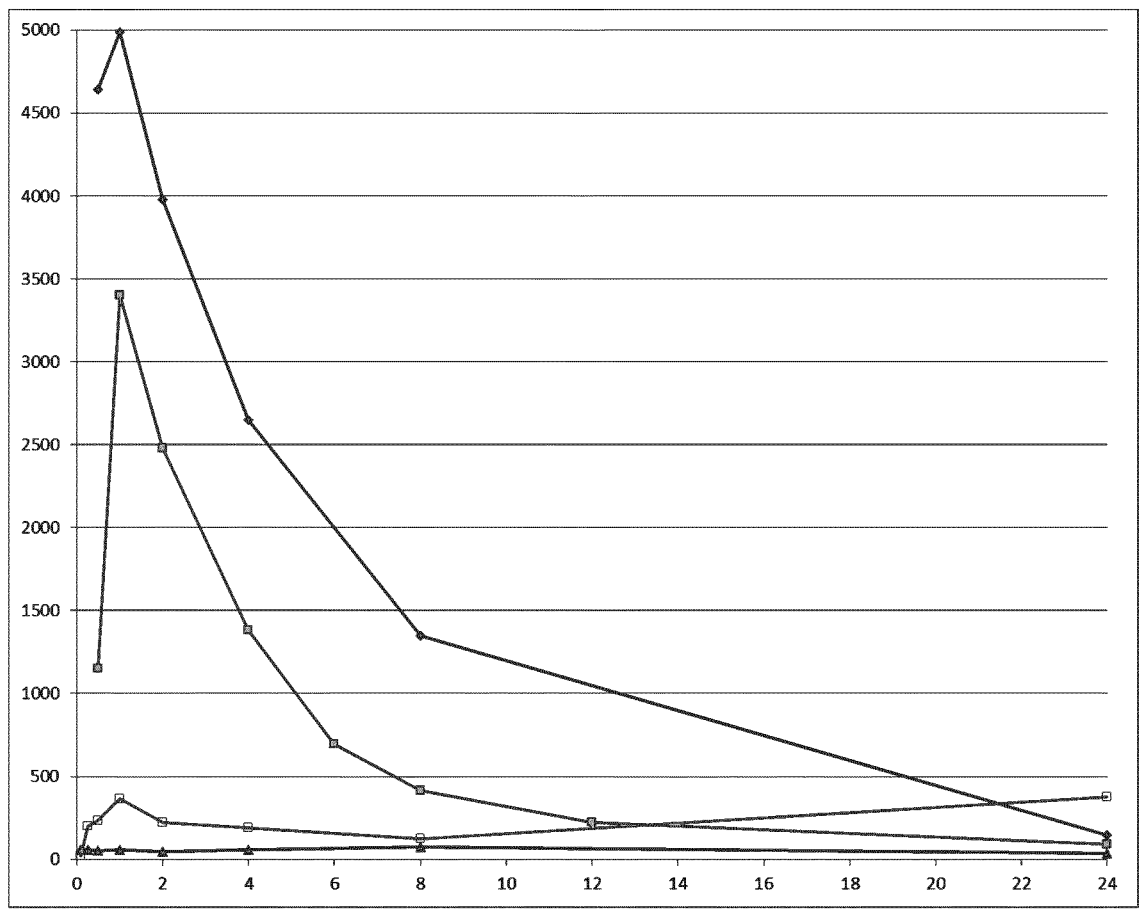

It has been found that oral dosing of compounds (Ia) and (Ib) to Wistar rats results in early and high peak plasma concentrations of compound (I). Such high peak concentrations are in humans likely to be associated with dopaminergic side effects such as for example nausea, vomiting and light headedness. In contrast, for the compounds of the invention a slower absorption rate was observed accompanied by a sustained exposure of compound (I) avoiding rapid peak plasma concentrations. Additionally, the plasma exposure of compound (I) in Wistar rats is maintained throughout 24 hours although the obtained AUC of compound (I) is generally lower than the AUC obtained after dosing of compounds (Ia) and (Ib). However, since the peak concentrations of compound (I) which are expected to drive the side effects are lower, higher doses of the compounds of the invention may be administered to potentially achieve higher overall plasma concentrations of compound (I) compared to what is achievable from dosing compounds (Ia) and (Ib). When investigating PK properties of compound (Ic), the inventors found that the plasma concentrations of compound (I) were extremely low, leaving compound (Ic) unsuitable as a prodrug of compound (I) for oral administration and confirming that the oral bioavailability of the compounds of the invention is highly unpredictable. PK parameters for the PK studies in Wistar rats are listed in Table 4 and PK profiles are depicted in FIG. 2. All the compounds evaluated in vivo showed conversion to compound (I).

Figure 1A:
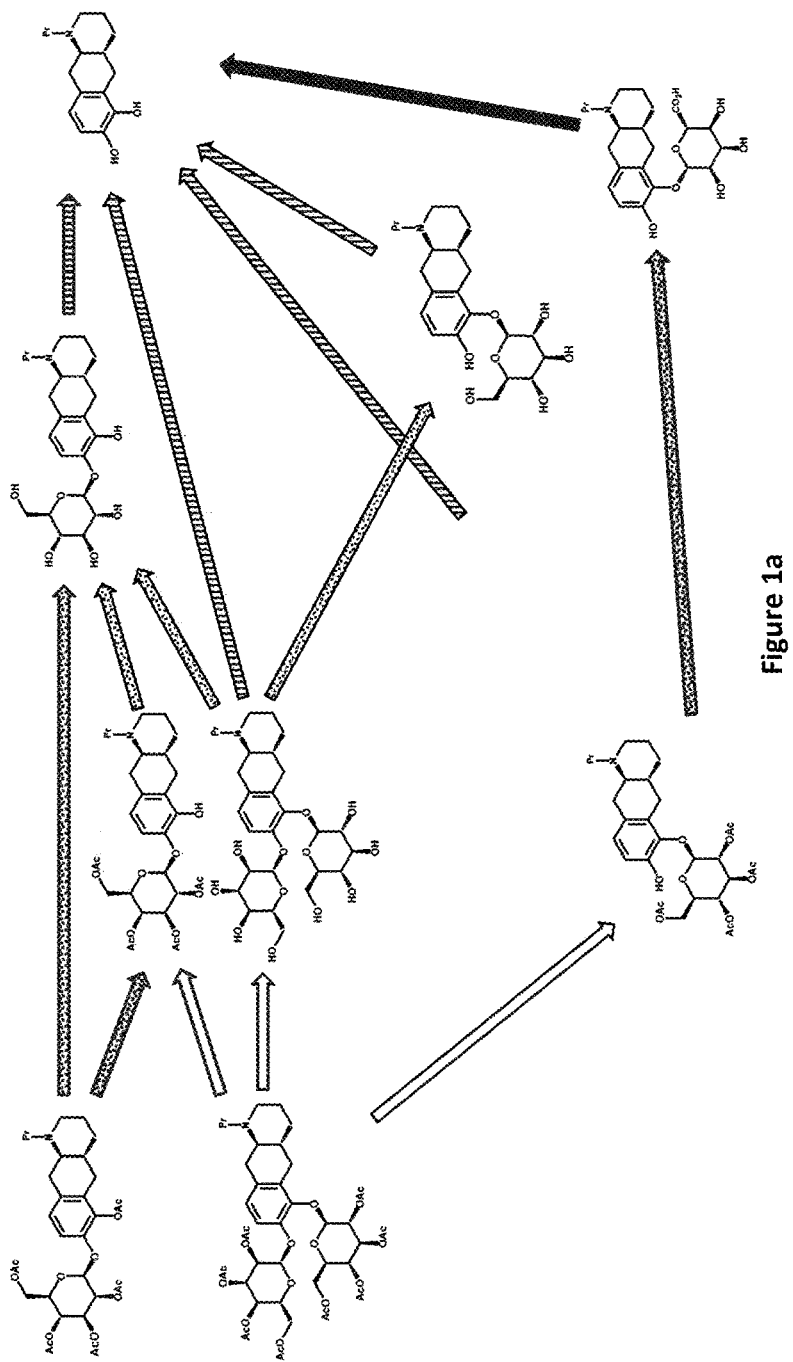
FIG. 1: graphic illustration of conversion of compounds of the invention to compound (Id).
Solid arrows: conversion demonstrated in vitro and in vivo. Dotted arrows: conversion demonstrate in vitro. Streaky arrows: conversion demonstrated in vivo.
Open arrows: conversion not demonstrated. The illustrations have been divided into FIGS. 1a and 1b to provide a better overview.
Figure 1B:
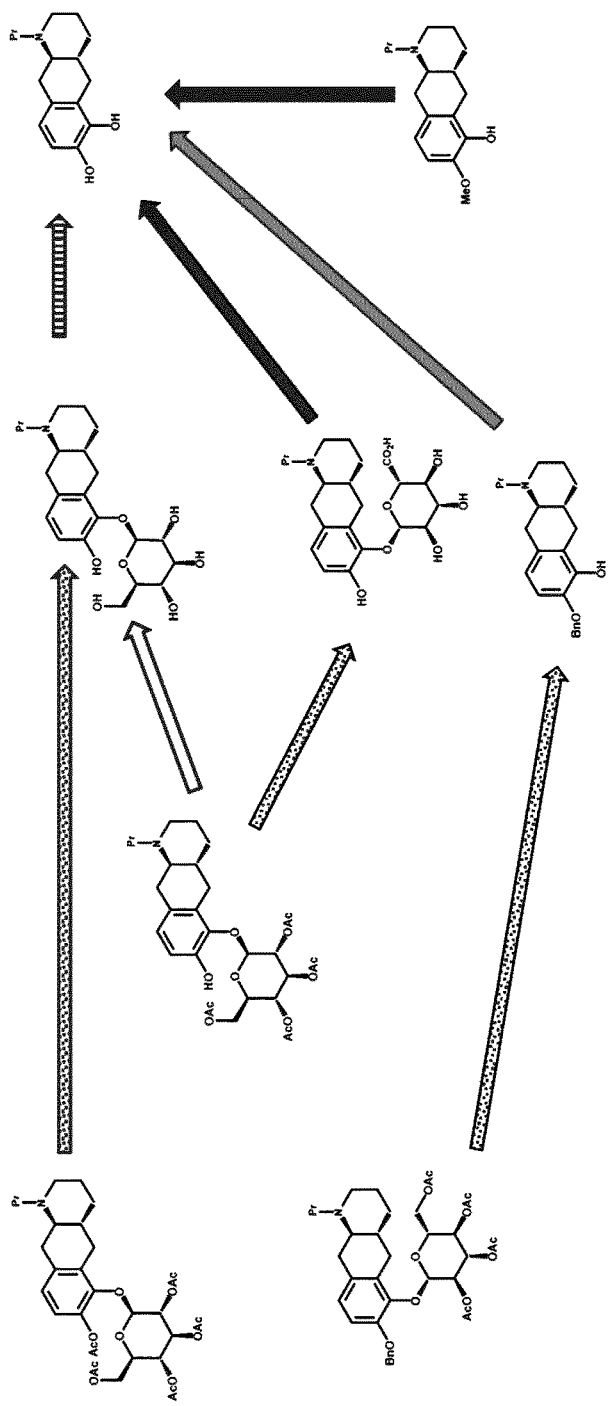

Bioconversion of the compounds of the invention to the compound of formula (I) has also been assessed by incubation in human plasma and/or human hepatocytes as described in Example 1. For the parent compound (I) itself a short half-life in the plasma assay was observed, which likely explains why appearance of compound (I) was in some instances difficult to detect or only detected in very small amounts as compound (I) may have been metabolised at the same time as it was formed. For example, compound (4) showed conversion in vivo while no appearance of compound (I) could be detected in vitro. For some of the compounds no direct appearance of compound (I) was observed in the in vitro study, but the diagrams of FIG. 1 make it reasonable to believe that these compounds are converted to compound (I). For example, compound (6) which is an acetylated glycoside derivative is converted to compound (7) which is converted to compound (I). Another example is compound (8) which is an acetylated bis-glycoside derivative. For this compound no in vitro conversion could be demonstrated (the compound has not been tested in vivo). However, when looking at the diagrams in FIG. 1 as a whole, it is reasonable to believe that compound (8) is converted to compound (I) via one or more of compounds (5), (9) and (2). For compound (2) plasma incubation showed conversion to a glucuronide derivative (see FIG. 1) which is a metabolite of compound (I) and has been tested for suitability as a prodrug in a separate assay and shown to be converted to compound (I) both in vitro and in vitro as described in WO2019/101917. Furthermore, again looking at the diagrams as a whole, it is plausible that compound (2) is converted to compound (I) via compound (4).

For compounds of the invention, conversion was evaluated either in vitro or both in vivo and in vitro c.f. Table 1 below and in FIG. 1.

TABLE 1

Observed metabolites in vivo and in vitro

| | Observed metabolite | | |
|---|---|---|---|
| | Incubation in human plasma | Incubation in human hepatocytes | In vivo PK study after oral dosing (rats) |
| Compound (4) | nd | Compound (I) | Compound (I) |
| Compound (2) | Glucuronide derivative of compound (I) | nd | nt |
| Compound (3) | nd | Compound (4) | nt |
| Compound (7) | nd | nd | nt |
| Compound (5) | Compound (7) | Compound (7) | nt |
| Compound (6) | Compound (7) and Compound (5) | Compound (7) and Compound (5) | nt |
| Compound (9) | Compound (7) | Compound (4) and Compound (7) | Compound (I) |
| Compound (8) | nd | nd | nt |
| A2 | Compound (I) | Compound (I) | Compound (I) |
| A6 | nd | Compound (I) | Compound (I) | nt: not tested
nd: not detected

The glycoside derivatives are preferred embodiments of the invention.

Thus, in conclusion, the compounds of the invention are useful as orally active prodrugs of compound (I) and has been observed in rats to provide a PK profile avoiding the peak $C_{max}$ observed for the known prodrugs (Ia) and (Ib) and providing a significantly higher AUC of compound (I) than compound (Ic).

Finally, an important issue associated with the prior art compound (Ib) is that this compound is an agonist of the 5-HT2B receptor. Since 5-HT2B receptor agonists have been linked to pathogenesis of valvular heart disease (VHD) after long term exposure, such compounds are not suitable for use in the treatment of chronical diseases (Rothman et al., Circulation (2000), 102: 2836-2841; and Cavero and Guillon, J. Pharmacol. Toxicol. Methods (2014), 69: 150-161). Thus, a further advantage of the compounds of the invention is that these are not 5-HT2B agonists c.f. example 2 and Table 3.

The compounds of the invention are useful in the treatment of neurodegenerative diseases and disorders such as Parkinson's disease and/or other conditions for which treatment with a dopamine agonist is therapeutically beneficial. The compounds, being suitable for oral administration have the potential of providing a new treatment paradigm in Parkinson's Disease.

In one embodiment of the invention, the compounds are for use as stand-alone treatment of a neurodegenerative disease or disorder. In another embodiment of the invention, the compounds are to be used in combination with other agents for treatment of PD such as a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

EMBODIMENTS OF THE INVENTION

In the following, embodiments of the invention are disclosed. The first embodiment is denoted E1, the second embodiment is denoted E2 and so forth E1. A compound according to formula (Id)

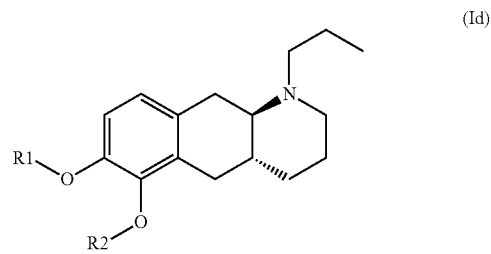

(Id)

wherein R1 and R2 are according to a) to c) below:
  a) R1 is selected from H, $C_1$-$C_6$ alkyl, benzyl and linear —C(O)$C_1$-$C_6$ alkyl and R2 is substituent (i) below; or
  b) R1 is substituent (i) below and R2 is selected from H, $C_1$-$C_6$ alkyl, benzyl and linear —C(O)$C_1$-$C_6$ alkyl; or
  c) R1 and R2 are both represented by substituent (i) below

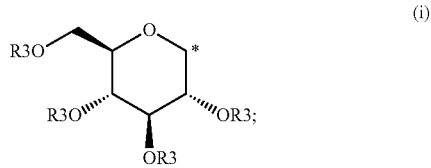

(i)

and wherein R3 is selected from H and —C(O)C$_1$-C$_6$ alkyl; and wherein * indicates the attachment point; and wherein the carbon atom at the attachment point on substituent (i) is in the S-configuration;

with the proviso that when one of R1 or R2 is substituent (i) and R3 is H then the other of R1 or R2 cannot be linear-C(O)C$_1$-C$_6$ alkyl;

or a pharmaceutically acceptable salt thereof.

E2. The compound or pharmaceutically acceptable salt thereof according to embodiment 1, wherein
R1 is selected from H, C$_1$-C$_6$ alkyl, benzyl and —C(O)C$_1$-C$_6$ alkyl; and R2 is substituent (i).

E3. The compound or pharmaceutically acceptable salt thereof according to embodiment 1, wherein
R1 is substituent (i) below; and R2 is selected from H, C$_1$-C$_6$ alkyl, benzyl and linear —C(O)C$_1$-C$_6$ alkyl.

E4. The compound or pharmaceutically acceptable salt thereof according to embodiment 1, wherein R1 and R2 are both represented by substituent (i).

E5. The compound or pharmaceutically acceptable salt thereof according to any of embodiments 1-4, wherein R1 or R2 is —C(O)methyl.

E6. The compound or pharmaceutically acceptable salt thereof according to any of embodiments 1-5, wherein R3 is —C(O)methyl.

E7. The compound or pharmaceutically acceptable salt thereof according to any of embodiments 1-5, wherein R3 is H.

E8. The compound or pharmaceutically acceptable salt thereof according to any of embodiments 1 and 5, wherein one of R1 and R2 is H and the other of R1 and R2 is substituent (i), and wherein R3 is H.

E9. The compound according to embodiment 1, wherein the compound is selected from the group consisting of:

Compound (1): (2R,3R,4S,5R,6S)-2-(acetoxymethyl)-6-(((4aR,10aR)-7-(benzyloxy)-1-propyl-1,2,3,4,4a,5,10,10a-octahydrobenzo[g]quinolin-6-yl)oxy)tetrahydro-2H-pyran-3,4,5-triyl triacetate;

Compound (2): (2R,3R,4S,5R,6S)-2-(acetoxymethyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate;

Compound (3): (2S,3R,4S,5R,6R)-2-(((4aR,10aR)-7-acetoxy-1-propyl-1,2,3,4,4a,5,10,10a-octahydrobenzo[g]quinolin-6-yl)oxy)-6-(acetoxymethyl)tetrahydro-2H-pyran-3,4,5-triyl triacetate;

Compound (4): (2S,3R,4S,5S,6R)-2-(((4aR,10aR)-7-hydroxy-1-propyl-1,2,3,4,4a,5,10,10a-octahydrobenzo[g]quinolin-6-yl)oxy)-6-(hydroxymethyl)tetrahydro-2H-pyran-3,4,5-triol;

Compound (5): (2R,3R,4S,5R,6S)-2-(acetoxymethyl)-6-(((4aR,10aR)-6-hydroxy-1-propyl-1,2,3,4,4a,5,10,10a-octahydrobenzo[g]quinolin-7-yl)oxy)tetrahydro-2H-pyran-3,4,5-triyl triacetate;

Compound (6): (2S,3R,4S,5R,6R)-2-(((4aR,10aR)-6-acetoxy-1-propyl-1,2,3,4,4a,5,10,10a-octahydrobenzo[g]quinolin-7-yl)oxy)-6-(acetoxymethyl)tetrahydro-2H-pyran-3,4,5-triyl triacetate;

Compound (7): (2S,3R,4S,5S,6R)-2-(((4aR,10aR)-6-hydroxy-1-propyl-1,2,3,4,4a,5,10,10a-octahydrobenzo[g]quinolin-7-yl)oxy)-6-(hydroxymethyl)tetrahydro-2H-pyran-3,4,5-triol;

Compound (8): [(2R,3R,4S,5R,6S)-6-[[(4aR,10aR)-1-propyl-6-[(2S,3R,4S,5R,6R)-3,4,5-triacetoxy-6-(acetoxymethyl)tetrahydropyran-2-yl]oxy-3,4,4a,5,10,10a-hexahydro-2H-benzo[g]quinolin-7-yl]oxy]-3,4,5-triacetoxytetrahydropyran-2-yl]methyl acetate; and Compound (9): (2R,2'R,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(2-(hydroxymethyl)tetrahydro-2H-pyran-3,4,5-triol);

or a pharmaceutically acceptable salt of any of these compounds.

E10. A compound selected from the group consisting of:

Compound (1): (2R,3R,4S,5R,6S)-2-(acetoxymethyl)-6-(((4aR,10aR)-7-(benzyloxy)-1-propyl-1,2,3,4,4a,5,10,10a-octahydrobenzo[g]quinolin-6-yl)oxy)tetrahydro-2H-pyran-3,4,5-triyl triacetate;

Compound (2): (2R,3R,4S,5R,6S)-2-(acetoxymethyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate;

Compound (3): (2S,3R,4S,5R,6R)-2-(((4aR,10aR)-7-acetoxy-1-propyl-1,2,3,4,4a,5,10,10a-octahydrobenzo[g]quinolin-6-yl)oxy)-6-(acetoxymethyl)tetrahydro-2H-pyran-3,4,5-triyl triacetate;

Compound (4): (2S,3R,4S,5S,6R)-2-(((4aR,10aR)-7-hydroxy-1-propyl-1,2,3,4,4a,5,10,10a-octahydrobenzo[g]quinolin-6-yl)oxy)-6-(hydroxymethyl)tetrahydro-2H-pyran-3,4,5-triol;

Compound (5): (2R,3R,4S,5R,6S)-2-(acetoxymethyl)-6-(((4aR,10aR)-6-hydroxy-1-propyl-1,2,3,4,4a,5,10,10a-octahydrobenzo[g]quinolin-7-yl)oxy)tetrahydro-2H-pyran-3,4,5-triyl triacetate;

Compound (6): (2S,3R,4S,5R,6R)-2-(((4aR,10aR)-6-acetoxy-1-propyl-1,2,3,4,4a,5,10,10a-octahydrobenzo[g]quinolin-7-yl)oxy)-6-(acetoxymethyl)tetrahydro-2H-pyran-3,4,5-triyl triacetate;

Compound (7): (2S,3R,4S,5S,6R)-2-(((4aR,10aR)-6-hydroxy-1-propyl-1,2,3,4,4a,5,10,10a-octahydrobenzo[g]quinolin-7-yl)oxy)-6-(hydroxymethyl)tetrahydro-2H-pyran-3,4,5-triol;

Compound (8): [(2R,3R,4S,5R,6S)-6-[[(4aR,10aR)-1-propyl-6-[(2S,3R,4S,5R,6R)-3,4,5-triacetoxy-6-(acetoxymethyl)tetrahydropyran-2-yl]oxy-3,4,4a,5,10,10a-hexahydro-2H-benzo[g]quinolin-7-yl]oxy]-3,4,5-triacetoxytetrahydropyran-2-yl]methyl acetate;

Compound (9): (2R,2'R,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(2-(hydroxymethyl)tetrahydro-2H-pyran-3,4,5-triol);

A2: (4aR,10aR)-7-(benzyloxy)-1-propyl-1,2,3,4,4a,5,10,10a-octahydrobenzo[g]quinolin-6-ol; and A6: (4aR,10aR)-7-methoxy-1-propyl-1,2,3,4,4a,5,10,10a-octahydrobenzo[g]quinolin-6-ol;

or a pharmaceutically acceptable salt of any of these compounds.

E11. A compound according to embodiment 1, wherein the compound is selected from the group consisting of:

Compound (4): (2S,3R,4S,5S,6R)-2-(((4aR,10aR)-7-hydroxy-1-propyl-1,2,3,4,4a,5,10,10a-octahydrobenzo[g]quinolin-6-yl)oxy)-6-(hydroxymethyl)tetrahydro-2H-pyran-3,4,5-triol;

Compound (7): (2S,3R,4S,5S,6R)-2-(((4aR,10aR)-6-hydroxy-1-propyl-1,2,3,4,4a,5,10,10a-octahydrobenzo[g]quinolin-7-yl)oxy)-6-(hydroxymethyl)tetrahydro-2H-pyran-3,4,5-triol; and Compound (9): (2R,2'R,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(2-(hydroxymethyl)tetrahydro-2H-pyran-3,4,5-triol);

or a pharmaceutically acceptable salt of any of these compounds.

E12. A compound of the following formula:

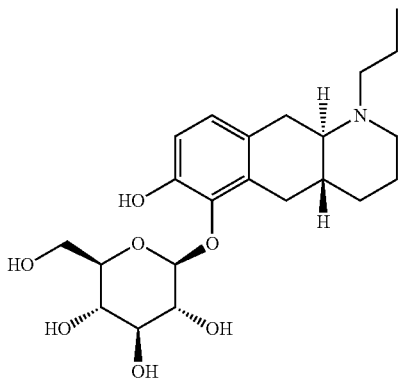 [SMILES: CCCN1CCC[C@@H]2Cc3c(ccc(O)c3O[C@@H]3O[C@H](CO)[C@@H](O)[C@H](O)[C@H]3O)C[C@H]21]

or a pharmaceutically acceptable salt thereof.

E13. A compound of the following formula:

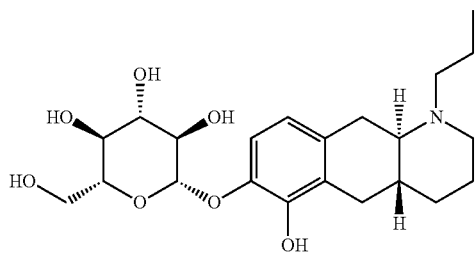 [SMILES: CCCN1CCC[C@@H]2Cc3c(ccc(O[C@@H]4O[C@H](CO)[C@@H](O)[C@H](O)[C@H]4O)c3O)C[C@H]21]

or a pharmaceutically acceptable salt thereof.

E14. A compound of the following formula:

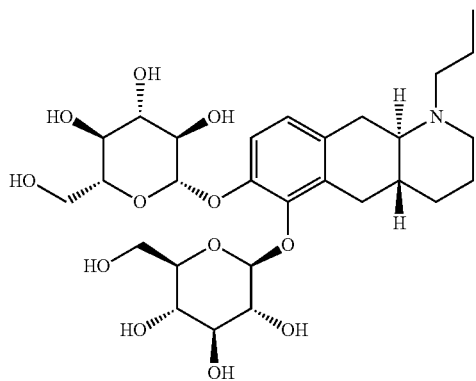 [SMILES: CCCN1CCC[C@@H]2Cc3c(ccc(O[C@@H]4O[C@H](CO)[C@@H](O)[C@H](O)[C@H]4O)c3O[C@@H]3O[C@H](CO)[C@@H](O)[C@H](O)[C@H]3O)C[C@H]21]

or a pharmaceutically acceptable salt thereof.

E15. A compound selected from the group consisting of:
A2: (4aR,10aR)-7-(benzyloxy)-1-propyl-1,2,3,4,4a,5,10,10a-octahydrobenzo[g]quinolin-6-ol; and
A6: (4aR,10aR)-7-methoxy-1-propyl-1,2,3,4,4a,5,10,10a-octahydrobenzo[g]quinolin-6-ol;
or a pharmaceutically acceptable salt of any of these compounds.

E16. A compound which is a prodrug of the compound (4aR,10aR)-1-Propyl-1,2,3,4,4a,5,10,10a-octahydro-benzo[g]quinoline-6,7-diol (compound (I)), wherein said prodrug provides a PK profile wherein $C_{max}$ of (4aR,10aR)-1-Propyl-1,2,3,4,4a,5,10,10a-octahydro-benzo[g]quinoline-6,7-diol is between 500 and 1500 pg/mL, such as between 750 and 1250 pg/mL, such as between 800 and 1200 pg/mL and $t_{max}$ is between 1.0 and 3.0 hours, such as between 1.2 and 2.8 hours, such as between 1.5 and 2.5 hours when said prodrug is administered orally to a Wistar rat in a dose corresponding to 287 pg/kg of (4aR,10aR)-1-Propyl-1,2,3,4,4a,5,10,10a-octahydro-benzo[g]quinoline-6,7-diol;
or a pharmaceutically acceptable salt of said compound.

E17. The compound or pharmaceutically acceptable salt thereof according to embodiment 16, which is a prodrug of the compound (4aR,10aR)-1-Propyl-1,2,3,4,4a,5,10,10a-octahydro-benzo[g]quinoline-6,7-diol (compound (I)), wherein said prodrug provides a PK profile wherein $AUC_{0-24}$ of (4aR,10aR)-1-Propyl-1,2,3,4,4a,5,10,10a-octahydro-benzo[g]quinoline-6,7-diol is more than more than 10000, such as more than 11000, such as more than 12000, such as more than 13000, such as more than 14000, such as more than 15000, such as more than 16000, such as more than 17000 pg*h/mL when said prodrug is administered orally to a Wistar rat in a dose corresponding to 287 mg/kg of (4aR,10aR)-1-Propyl-1,2,3,4,4a,5,10,10a-octahydro-benzo[g]quinoline-6,7-diol.

E18. The compound or pharmaceutically acceptable salt thereof according to any of embodiments 16-17, wherein said PK profile has been obtained by a PK experiment as described in Example 3 herein.

E19. The compound or pharmaceutically acceptable salt thereof according to any of embodiments 1-18, for use in therapy.

E20. A compound or pharmaceutically acceptable salt thereof according to any of embodiments 1-18, for use as a medicament.

E21. The compound or pharmaceutically acceptable salt for use as a medicament according to embodiment 20, wherein said medicament is an oral medicament such as a tablet or a capsule for oral administration.

E22. A pharmaceutical composition comprising a therapeutically effective amount of the compound or pharmaceutically acceptable salt thereof according to any of embodiments 1-18, and one or more pharmaceutically acceptable excipients.

E23. The pharmaceutical composition according to embodiment 22, wherein said pharmaceutical composition is for oral administration.

E24. The pharmaceutical composition according to any of embodiments 22-23, wherein said pharmaceutical composition is an oral pharmaceutical composition.

E25. The pharmaceutical composition according to any of embodiments 22-24, wherein said pharmaceutical composition is a solid oral dosage form.

E26. The pharmaceutical composition according to any of embodiments 22-25, wherein said pharmaceutical composition is a tablet or a capsule for oral administration.

E27. The pharmaceutical composition according to any of embodiments 22-26, wherein said pharmaceutical composition further comprises another agent which is useful in the treatment of a neurodegenerative disease or disorder such as Parkinson's disease.

E28. The pharmaceutical composition according to any of embodiments 22-27, wherein said pharmaceutical composition further comprises a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or an antibody targeting alpha-synuclein, Tau or A-beta protein.

E29. A compound or pharmaceutically acceptable salt thereof according to any of embodiments 1-18, for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

E30. The compound or pharmaceutically acceptable salt thereof according to any of embodiments 1-18, for use in the treatment according to embodiment 29, wherein said neurodegenerative disease or disorder is Parkinson's Disease.

E31. The compound or pharmaceutically acceptable salt thereof according to any of embodiments 1-18, for use in the treatment according to any of embodiments 29-30, wherein said compound is to be used in combination with another agent which is useful in the treatment of a neurodegenerative disease or disorder such as Parkinson's disease.

E32. The compound or pharmaceutically acceptable salt thereof according to any of embodiments 1-18, for use in the treatment according to any of embodiments 29-31, wherein said compound is to be used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E33. The compound or pharmaceutically acceptable salt thereof according to any of embodiments 1-18, for use in the treatment according to any of embodiments 29-32, wherein said treatment is performed by oral administration of said compound.

E34. The compound or pharmaceutically acceptable salt thereof according to any of embodiments 1-18, for use in the treatment according to any of embodiments 29-33, wherein said compound is comprised in an oral pharmaceutical composition such as a tablet or a capsule for oral administration.

E35. A method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound or pharmaceutically acceptable salt thereof according to any of embodiments 1-18, to a patient in need thereof.

E36. The method according to embodiment 35, wherein said neurodegenerative disease or disorder is Parkinson's Disease.

E37. The method according to any of embodiments 35-36, wherein said compound or pharmaceutically acceptable salt thereof according to any of embodiments 1-18, is used in combination with another agent which is useful in the treatment of a neurodegenerative disease or disorder such as Parkinson's disease.

E38. The method according to any of embodiments 35-37, wherein said compound or pharmaceutically acceptable salt thereof according to any of embodiments 1-18, is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E39. The method according to any of embodiments 35-38, wherein said administration is performed by the oral route.

E40. The method according to any of embodiments 35-39, wherein said compound or pharmaceutically acceptable salt thereof according to any of embodiments 1-18 is comprised in an oral pharmaceutical composition such as a tablet or a capsule for oral administration.

E41. Use of a compound or pharmaceutically acceptable salt thereof according to any of embodiments 1-18, in the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

E42. The use according to embodiment 41, wherein said neurodegenerative disease or disorder is Parkinson's Disease.

E43. The use according to any of embodiments 41-42, wherein said medicament is used in combination with another agent which is useful in the treatment of a neurodegenerative disease or disorder such as Parkinson's disease.

E44. The use according to any of embodiments 41-43, wherein said medicament is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E45. The use according to any of embodiments 41-44, wherein said medicament is an oral medicament such as a tablet or a capsule for oral administration.

In the context of the present invention, it is understood that the carbon atom at the attachment point on substituent (i) (depicted in embodiment 1) is at the anomeric position of (i).

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (including "for instance", "for example", "e.g.", "such as" and "as such") in the present specification is intended merely to better illuminate the invention, and does not pose a limitation on the scope of invention unless otherwise indicated.

It should be understood that the various aspects, embodiments, implementations and features of the invention mentioned herein may be claimed separately, or in any combination.

The present invention includes all modifications and equivalents of the subject-matter recited in the claims appended hereto, as permitted by applicable law.

COMPOUNDS OF THE INVENTION

TABLE 2

Exemplified compounds of the invention

| Example | Compound name | Structure |
| --- | --- | --- |
| Compound (1) | (2R,3R,4S,5R,6S)-2-(acetoxymethyl)-6-(((4aR,10aR)-7-(benzyloxy)-1-propyl-1,2,3,4,4a,5,10,10a-octahydrobenzo[g]quinolin-6-yl)oxy)tetrahydro-2H-pyran-3,4,5-triyl triacetate | 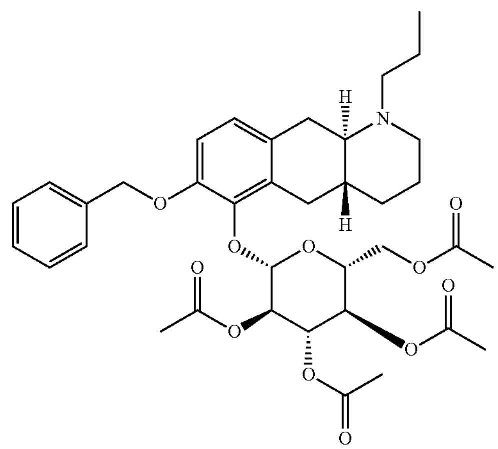 [SMILES: CCCN1CCC[C@@H]2Cc3c(ccc(OCc4ccccc4)c3O[C@@H]3O[C@H](COC(C)=O)[C@@H](OC(C)=O)[C@H](OC(C)=O)[C@H]3OC(C)=O)C[C@H]21] |
| Compound (2) | (2R,3R,4S,5R,6S)-2-(acetoxymethyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate | 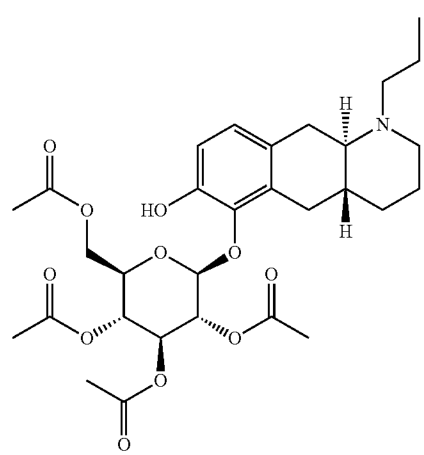 [SMILES: CCCN1CCC[C@@H]2Cc3c(ccc(O)c3O[C@@H]3O[C@H](COC(C)=O)[C@@H](OC(C)=O)[C@H](OC(C)=O)[C@H]3OC(C)=O)C[C@H]21] |

TABLE 2-continued

Exemplified compounds of the invention

| Example | Compound name | Structure |
|---|---|---|
| Compound (3) | (2S,3R,4S,5R,6R)-2-(((4aR,10aR)-7-acetoxy-1-propyl-1,2,3,4,4a,5,10,10a-octahydrobenzo[g]quinolin-6-yl)oxy)-6-(acetoxymethyl)tetrahydro-2H-pyran-3,4,5-triyl triacetate | 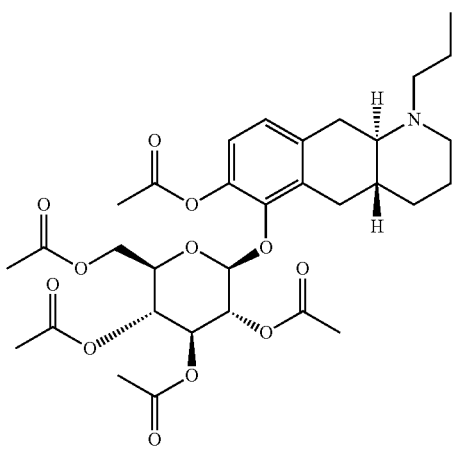 [SMILES: CCCN1CCC[C@@H]2Cc3c(ccc(OC(C)=O)c3O[C@@H]3O[C@H](COC(C)=O)[C@@H](OC(C)=O)[C@H](OC(C)=O)[C@H]3OC(C)=O)C[C@H]21] |
| Compound (4) | (2S,3R,4S,5S,6R)-2-(((4aR,10aR)-7-hydroxy-1-propyl-1,2,3,4,4a,5,10,10a-octahydrobenzo[g]quinolin-6-yl)oxy)-6-(hydroxymethyl)tetrahydro-2H-pyran-3,4,5-triol | 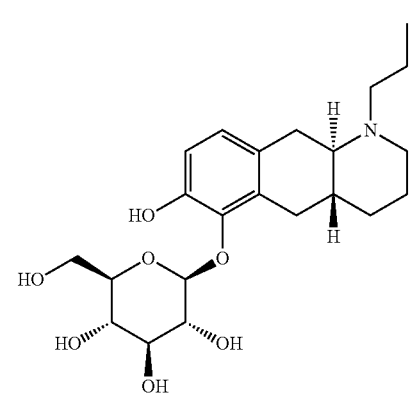 [SMILES: CCCN1CCC[C@@H]2Cc3c(ccc(O)c3O[C@@H]3O[C@H](CO)[C@@H](O)[C@H](O)[C@H]3O)C[C@H]21] |
| Compound (5) | (2R,3R,4S,5R,6S)-2-(acetoxymethyl)-6-(((4aR,10aR)-6-hydroxy-1-propyl-1,2,3,4,4a,5,10,10a-octahydrobenzo[g]quinolin-7-yl)oxy)tetrahydro-2H-pyran-3,4,5-triyl triacetate | 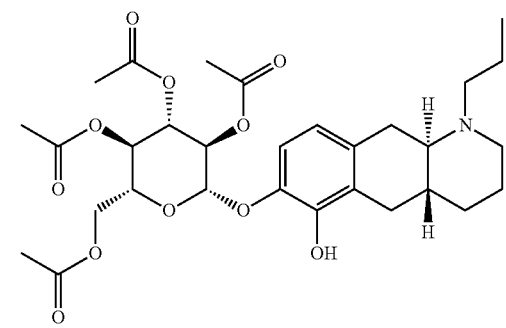 [SMILES: CCCN1CCC[C@@H]2Cc3c(ccc(O[C@@H]4O[C@H](COC(C)=O)[C@@H](OC(C)=O)[C@H](OC(C)=O)[C@H]4OC(C)=O)c3O)C[C@H]21] |
| Compound (6) | (2S,3R,4S,5R,6R)-2-(((4aR,10aR)-6-acetoxy-1-propyl-1,2,3,4,4a,5,10,10a-octahydrobenzo[g]quinolin-7-yl)oxy)-6-(acetoxymethyl)tetrahydro-2H-pyran-3,4,5-triyl triacetate | 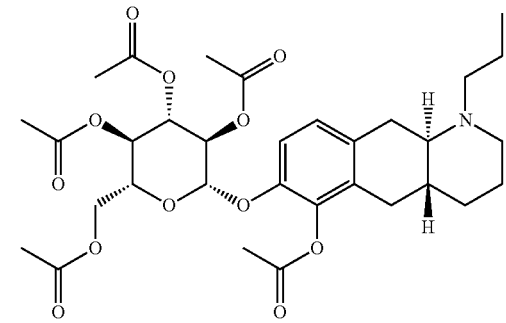 [SMILES: CCCN1CCC[C@@H]2Cc3c(ccc(O[C@@H]4O[C@H](COC(C)=O)[C@@H](OC(C)=O)[C@H](OC(C)=O)[C@H]4OC(C)=O)c3OC(C)=O)C[C@H]21] |

TABLE 2-continued

Exemplified compounds of the invention

| Example | Compound name | Structure |
|---|---|---|
| Compound (7) | (2S,3R,4S,5S,6R)-2-(((4aR,10aR)-6-hydroxy-1-propyl-1,2,3,4,4a,5,10,10a-octahydrobenzo[g]quinolin-7-yl)oxy)-6-(hydroxymethyl)tetrahydro-2H-pyran-3,4,5-triol | 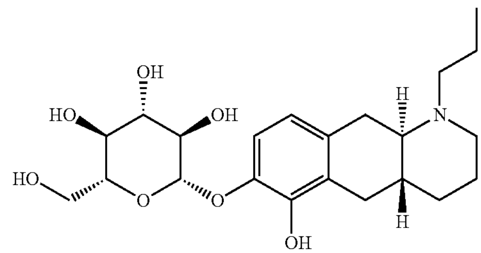 [SMILES: CCCN1CCC[C@@H]2Cc3c(ccc(O[C@@H]4O[C@H](CO)[C@@H](O)[C@H](O)[C@H]4O)c3O)C[C@H]21] |
| Compound (8) | [(2R,3R,4S,5R,6S)-6-[[(4aR,10aR)-1-propyl-6-[(2S,3R,4S,5R,6R)-3,4,5-triacetoxy-6-(acetoxymethyl)tetrahydropyran-2-yl]oxy-3,4,4a,5,10,10a-hexahydro-2H_benzo[g]quinolin-7-yl]oxy]-3,4,5-triacetoxy-tetrahydropyran-2-yl]methyl-acetate | 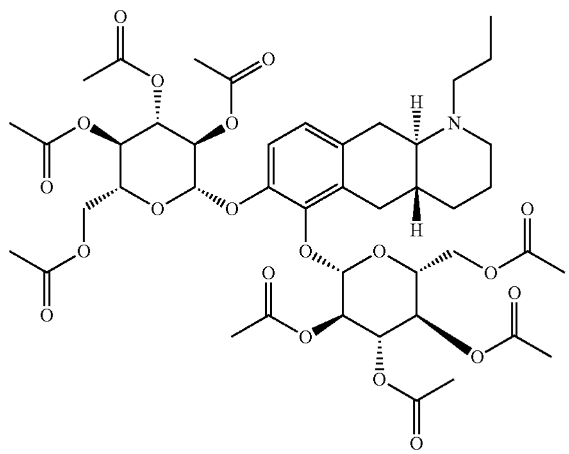 [SMILES: CCCN1CCC[C@@H]2Cc3c(ccc(O[C@@H]4O[C@H](COC(C)=O)[C@@H](OC(C)=O)[C@H](OC(C)=O)[C@H]4OC(C)=O)c3O[C@@H]3O[C@H](COC(C)=O)[C@@H](OC(C)=O)[C@H](OC(C)=O)[C@H]3OC(C)=O)C[C@H]21] |
| Compound (9) | (2R,2'R,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(2-(hydroxymethyl)tetrahydro-2H-pyran-3,4,5-triol) | 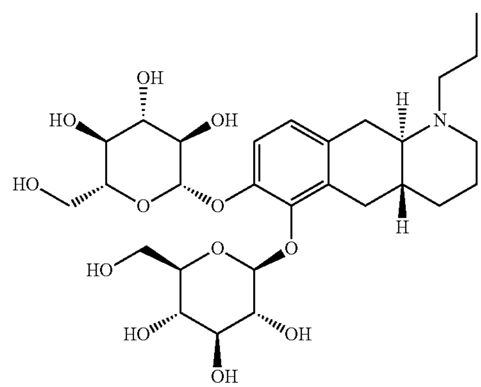 [SMILES: CCCN1CCC[C@@H]2Cc3c(ccc(O[C@@H]4O[C@H](CO)[C@@H](O)[C@H](O)[C@H]4O)c3O[C@@H]3O[C@H](CO)[C@@H](O)[C@H](O)[C@H]3O)C[C@H]21] |
| A2 | (4aR,10aR)-7-(benzyloxy)-1-propyl-1,2,3,4,4a,5,10,10a-octahydrobenzo[g]quinolin-6-ol | 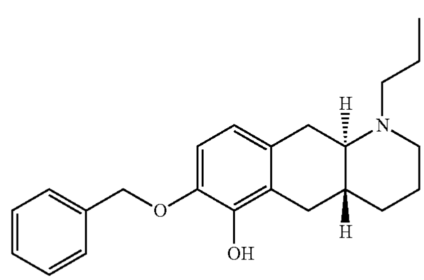 [SMILES: CCCN1CCC[C@@H]2Cc3c(ccc(OCc4ccccc4)c3O)C[C@H]21] |

TABLE 2-continued

Exemplified compounds of the invention

| Example | Compound name | Structure |
|---|---|---|
| A6 | (4aR,10aR)-7-methoxy-1-propyl-1,2,3,4,4a,5,10,10a-octahydrobenzo[g]quinolin-6-ol | 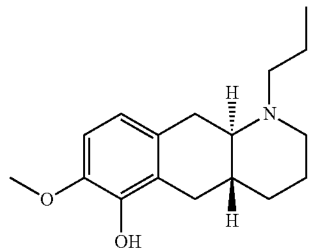 [SMILES: CCCN1CCC[C@@H]2Cc3c(ccc(OC)c3O)C[C@H]21] |

EXPERIMENTAL SECTION

Preparation of the Compounds of the Invention

The compounds of formula (Id) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XII" (published with Wiley-Interscience). Preferred methods include, but are not limited to, those described below.

The schemes are representative of methods useful in synthesizing the compounds of the present invention. They are not intended to constrain the scope of the invention in any way.

LC-MS Methods

Analytical LC-MS data were obtained using the methods identified below.

Method 25:
- MS: Ion source: (APPI), Temp 450° C. OR/RNG 20/200 V OR/RNG 5/100 V
- Mass: 100-1000 amu
- HPLC: Column: dC-18 4.6×30 mm 3 µm Atlantis (Waters)
- Column temperature: 40° C., Gradient, reverse phase with ion pairing
- Solvent A: 100% H2O 0.05% TFA
- Solvent B: 95% ACN 5% H2O 0.035% TFA
- Flow: 3.3 ml/min, Injection vol: 15 µL
- Gradient: 2% B to 100% B in 2.4 min, 2% B 0.4 min, Total run time: 2.8 minutes, UV: 254 nm.
- ELSD: Glass tube: 21° C., Evaporation chamber: 40° C., pressure: 2.3 bar.

Method 550:

LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 µm; 2.1×50 mm operating at 60° C. with 1.2 mL/min of a binary gradient consisting of water+0.05% trifluoroacetic acid (A) and acetonitrile/water (95:5)+0.05% trifluoroacetic acid.

Gradient:

| | |
|---|---|
| 0.00 min | 10% B |
| 1.00 min | 100% B |
| 1.01 min | 10% B |
| 1.15 min | 10% B |
| Total run time: 1.15 minutes | |

Method 10-90AB (Shimadzu LC-20AD&MS 2010):

| | |
|---|---|
| Method name: | 10-90AB |
| Instrument: | Shimadzu LC-20AD & MS 2020 |
| MS Mode: | Positive |
| MS Range: | 100-1000 |
| CDL Temp | 250° C. |
| Heat block Temp | 28° C. |
| Nebulizing gas flow | 1.5 L/min |

LC-conditions: the column was a Luna-C18(2) 2.0×30 mm, (3 micro particles) operated at 40° C. with 0.8 mL/min (0.01-1.51 min) and 1.2 mL/min (1.52-2.00 min) of a gradient of water+0.037% TFA (A) and MeCN+0.018% TFA (B).

Gradient:

| | |
|---|---|
| 0.01 min | 10% B |
| 0.01-1.15 min | 10-90% B |
| 1.15-1.65 min | 90% B |
| 1.65-1.66 min | 90-10% B |
| 1.66-2.00 min | 10% B |
| Total run time: 2.00 minutes | |

Method AB10 (Agilent 1200 & 1956A):

| | |
|---|---|
| Instrument: | Agilent 1200 & MS 1956A |
| MS Mode: | Positive |
| MS Range: | 100-1000 |
| MS Fragmentor | 70 V |
| Drying Gas Flow | 12 L/min |
| Nebulizer Pressure | 55 psig |
| Drying Gas Temp | 350° C. |
| Capillary Voltage | 2500 V |

LC-conditions: the column was a Luna-C18(2) 2.0×50 mm, 5 µm operated at 40° C. with 0.8 mL/min of a gradient of water+0.037% TFA (A) and MeCN+0.018% TFA (B).

Gradient:

| | |
|---|---|
| 0.00 min | 10% B |
| 0.01-0.40 min | 10% B |
| 0.40-3.40 min | 10-100% B |
| 3.40-3.85 min | 100% B |
| 3.85-3.86 min | 100-10% B |
| 3.86-4.50 min | 10% B |
| Total run time: 4.50 minutes | |

Method AB01 (Agilent 1200 & 6120):

| | |
|---|---|
| Instrument: | Agilent 1200 & MS 6120 |
| MS Mode: | Positive |
| MS Range: | 100-1000 |
| MS Fragmentor | 70 V |
| Drying Gas Flow | 12 L/min |
| Nebulizer Pressure | 40 psig |
| Drying Gas Temp | 350° C. |
| Capillary Voltage | 3500 V |

LC-conditions: the column was a Luna-C18(2) 2.0×50 mm, 5 μm operated at 40° C. with 0.8 mL/min of a gradient of water+0.037% TFA (A) and MeCN+0.018% TFA (B). Gradient:

| | |
|---|---|
| 0.00 min | 1% B |
| 0.01-0.40 min | 1% B |
| 0.40-3.40 min | 1-90% B |
| 3.40-3.85 min | 90-100% B |
| 3.85-3.86 min | 100-1% B |
| 3.86-4.50 min | 1% B |
| Total run time: 4.50 minutes | |

Method DELIVER-K (Agilent 1200 & 6110):

| | |
|---|---|
| Instrument: | Agilent 1200 & MS 6110 |
| MS Mode: | Positive |
| MS Range: | 100-1000 |
| MS Fragmentor | 70 V |
| Drying Gas Flow | 12 L/min |
| Nebulizer Pressure | 40 psig |
| Drying Gas Temp | 350° C. |
| Capillary Voltage | 2500 V |

LC-conditions: the column was a Halo-C18 3.0×30 mm, 2.7 μm operated at 40° C. with 0.8 mL/min of a gradient of water+0.037% TFA (A) and MeCN+0.018% TFA (B). Gradient:

| | |
|---|---|
| 0.01 min | 5% B |
| 0.01-1.60 min | 5-95% B |
| 1.60-2.50 min | 95-100% B |
| 2.50-2.52 min | 100-5% B |
| 2.52-3.00 min | 5% B |
| Total run time: 3.00 minutes | |

Method AB25—MS1500 (Agilent 1200 & 1956A):

| | |
|---|---|
| Instrument: | Agilent 1200 & MS 1956A |
| MS Mode: | Positive |
| MS Range: | 100-1500 |
| MS Fragmentor | 70 V |
| Drying Gas Flow | 12 L/min |
| Nebulizer Pressure | 55 psig |
| Drying Gas Temp | 350° C. |
| Capillary Voltage | 2500 V |

LC-conditions: the column was a Luna-C18(2) 2.0×50 mm, 5 μm operated at 40° C. with 0.8 mL/min of a gradient of water+0.037% TFA (A) and MeCN+0.018% TFA (B). Gradient:

| | |
|---|---|
| 0.00 min | 25% B |
| 0.01-0.40 min | 25% B |
| 0.40-3.40 min | 25-100% B |
| 3.40-3.85 min | 100% B |
| 3.85-3.86 min | 100-25% B |
| 3.86-4.50 min | 25% B |
| Total run time: 4.50 minutes | |

Method AB00 (Agilent 1200 & 1956A):

| | |
|---|---|
| Instrument: | Agilent 1260 & MS 6120 |
| MS Mode: | Positive |
| MS Range: | 100-1000 |
| MS Fragmentor | 70 V |
| Drying Gas Flow | 12 L/min |
| Nebulizer Pressure | 40 psig |
| Drying Gas Temp | 350° C. |
| Capillary Voltage | 2500 V |

LC-conditions: the column was a Luna-C18(2) 2.0×50 mm, 5 μm operated at 40° C. with 0.6 mL/min of a gradient of water+0.037% TFA (A) and MeCN+0.018% TFA (B). Gradient:

| | |
|---|---|
| 0.00 min | 0% B |
| 0.01-0.40 min | 0% B |
| 0.40-3.40 min | 0-80% B |
| 3.40-3.85 min | 80-100% B |
| 3.85-3.86 min | 100-0% B |
| 3.86-4.50 min | 0% B |
| Total run time: 4.50 minutes | |

Abbreviations of Chemical Ingredients

Ac: Acetyl
AcOH: Acetic acid
ACl: Acetyl chloride
ACN: Acetonitrile
$BF_3$—$OEt_2$: Boron trifluoride diethyl etherate
Bn: Benzyl
BnCl: Benzyl chloride
DCM: Dichloromethane
DIPEA: Diisopropylethyl amine
DMF: Dimethylformamide
EtOAc: Ethyl acetate
Me: Methyl
MeI: Methyl iodide
MeOH: Methanol
MeCN: Acetonitrile
MOM: Methoxymethyl
MOMCl: Methoxymethyl chloride
MS: Molecular sieves
Pd/C: Palladium on carbon
TFA: Trifluoroacetic acid
THF: Tetrahydrofuran
TMSCH2N2: Trimethylsilyl diazomethane
TMSI: Trimethylsilyl iodide

Preparation of Compounds of the Invention—General Methods (4aR,10aR)-1-Propyl-1,2,3,4,4a,5,10,10a-octahydrobenzo[g]quinoline-6,7-diol hydrochloride [Compound (I)] which can for example be prepared as disclosed in WO 2009/026934 was used as a substrate to synthesize of compounds of the invention.

Prodrugs with both catechol hydroxyl groups are linked to a glycosyl group can be prepared from (4aR,10aR)-1-propyl-1,2,3,4,4a,5,10,10a-octahydrobenzo[g]quinoline-6,7-diol by reaction with excess of a glycosyl donor such as (2R,3R,4S,5R,6R)-2-(acetoxymethyl)-6-(2,2,2-trichloro-1-iminoethoxy)tetrahydro-2H-pyran-3,4,5-triyl triacetate in the presence of a Lewis acid such as $BF_3$—$OEt_2$. This is illustrated in the scheme below wherein R3 is an ester group. Subsequent saponification with alkali hydroxide will afford the unprotected bis-glycoside as described herein for (2R,2'R,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(2-(hydroxymethyl)tetrahydro-2H-pyran-3,4,5-triol). In a similar manner using less of the glycosyl donor, one can prepare the compounds of the invention wherein the catechol 7-hydroxyl group is an esterified or unprotected glycoside. An ester group can be introduced on the free catechol hydroxyl in protected mono-glycosides by reaction with an acyl halide as described herein for (2S,3R,4S,5R,6R)-2-(((4aR,10aR)-6-acetoxy-1-propyl-1,2,3,4,4a,5,10,10a-octahydrobenzo[g]quinolin-7-yl)oxy)-6-(acetoxymethyl)tetrahydro-2H-pyran-3,4,5-triyl triacetate (wherein R3=Ac and R2=Me).

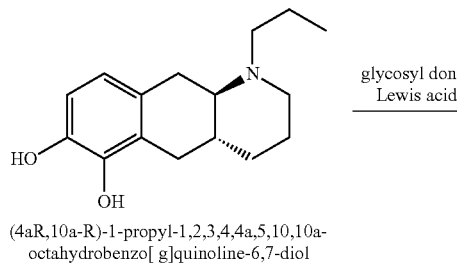

(4aR,10a-R)-1-propyl-1,2,3,4,4a,5,10,10a-octahydrobenzo[g]quinoline-6,7-diol

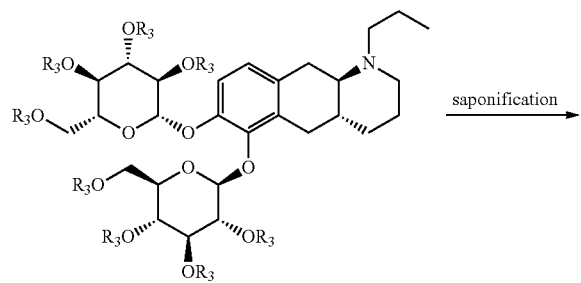

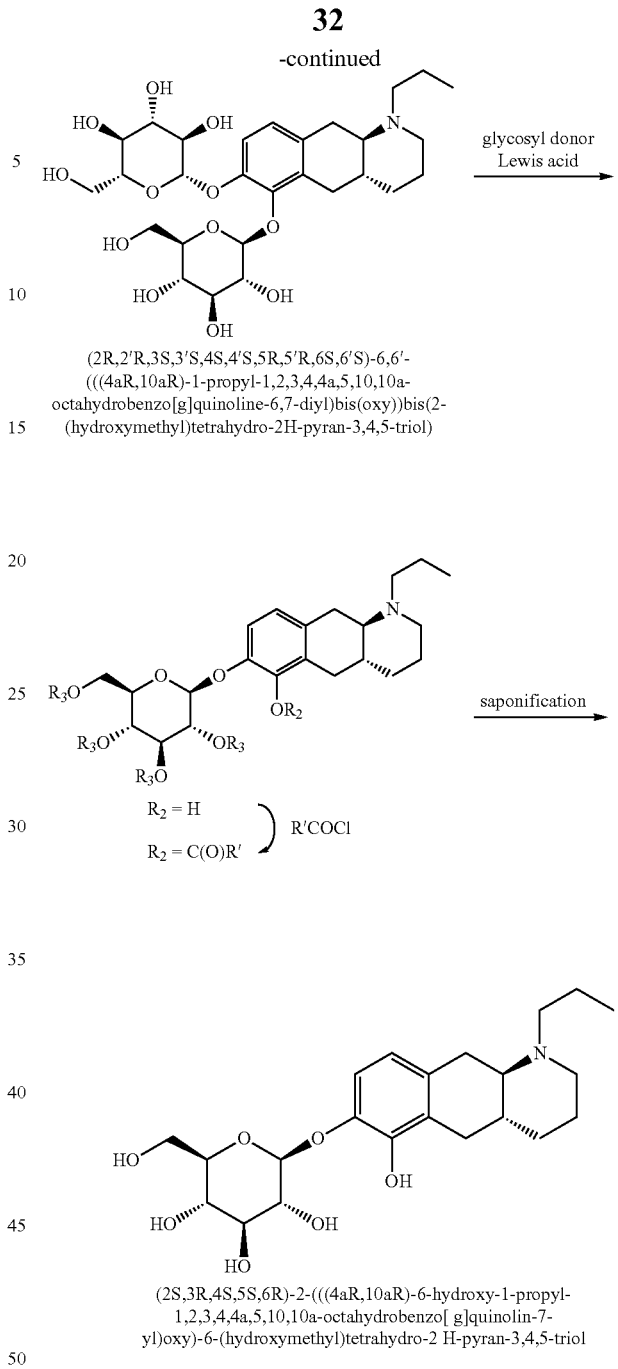

(2R,2'R,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(2-(hydroxymethyl)tetrahydro-2H-pyran-3,4,5-triol)

(2S,3R,4S,5S,6R)-2-(((4aR,10aR)-6-hydroxy-1-propyl-1,2,3,4,4a,5,10,10a-octahydrobenzo[g]quinolin-7-yl)oxy)-6-(hydroxymethyl)tetrahydro-2H-pyran-3,4,5-triol Analogs where the 6-catechol hydroxyl group is glycosylated and the 7-catechol hydroxyl is unsubstituted can be accessed from (4aR,10aR)-7-(benzyloxy)-1-propyl-1,2,3,4,4a,5,10,10a-octahydrobenzo[g]quinolin-6-ol by glycosidation followed by hydrogenolysis as outlined below (described herein for (2R,3R,4S,5R,6S)-2-(acetoxymethyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate). Saponification will afford the unprotected glycoside, while the group on the 7-catechol hydroxyl group can be manipulated after the hydrogenolysis step as shown below (and exemplified for (2S,3R,4S,5R,6R)-2-(((4aR,10aR)-7-acetoxy-1-propyl-1,2,3,4,4a,5,10,10a-octahydrobenzo[g]quinolin-6-yl)oxy)-6-(acetoxymethyl)tetrahydro-2H-pyran-3,4,5-triyl triacetate) wherein R3=Ac, R1=Ac.

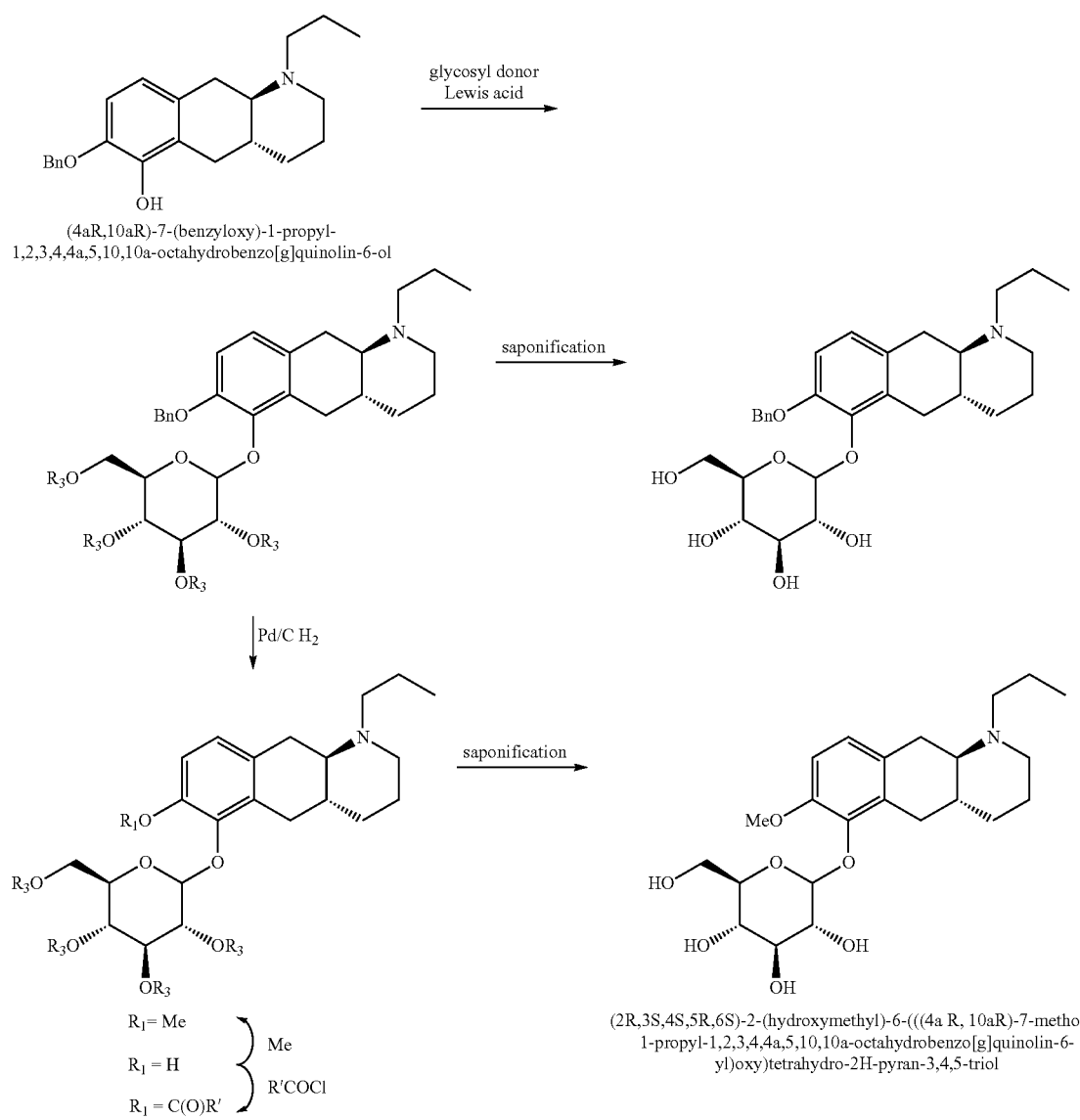

An alternative route from (4aR,10aR)-7-methoxy-1-propyl-1,2,3,4,4a,5,10,10a-octahydrobenzo[g]quinolin-6-ol to (2R,3S,4S,5R,6S)-2-(hydroxymethyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triol and analogs thereof with different ester groups on the four glycoside hydroxyl groups is illustrated below. Glycosidation gives ester-protected glycosides, which can be unmasked by saponification. Subsequent acylation would install different ester groups on the glycoside. Starting from (4aR,10aR)-7-(benzyloxy)-1-propyl-1,2,3,4,4a,5,10,10a-octahydrobenzo[g]quinolin-6-ol would afford the corresponding analogs wherein the methyl ether is replaced with a benzyl ether. It is further evident that using the regioisomeric substrates (i.e., (4aR,10aR)-6-methoxy-1-propyl-1,2,3,4,4a,5,10,10a-octahydrobenzo[g]quinolin-7-ol or (4aR,10aR)-6-(benzyloxy)-1-propyl-1,2,3,4,4a,5,10,10a-octahydrobenzo[g]quinolin-7-ol)) provides access to the 'opposite' glycosides, which are also accessible from the corresponding protected mono-glycosides using the general chemistry described above.

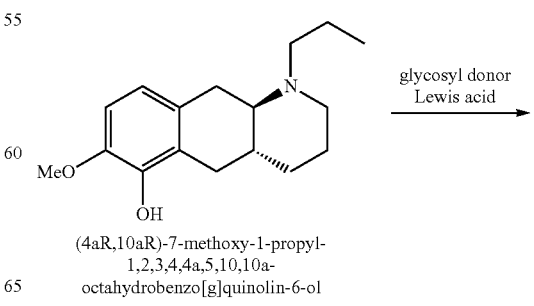

(4aR,10aR)-7-methoxy-1-propyl-1,2,3,4,4a,5,10,10a-octahydrobenzo[g]quinolin-6-ol -continued

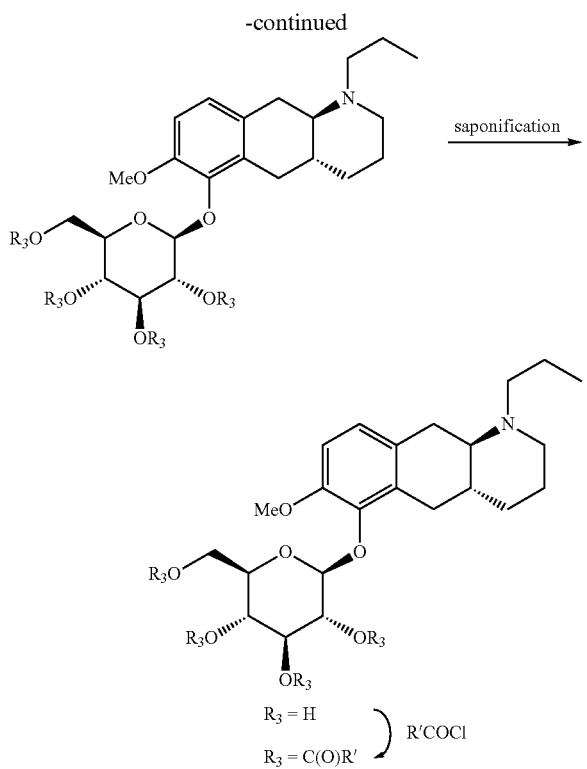

Treatment of compound (I) with BnCl and a base such as triethyl amine or K₂CO₃ will afford a mixture of (4aR,10aR)-6-(benzyloxy)-1-propyl-1,2,3,4,4a,5,10,10a-octahydrobenzo[g]quinolin-7-ol and (4aR,10aR)-7-(benzyloxy)-1-propyl-1,2,3,4,4a,5,10,10a-octahydrobenzo[g]quinolin-6-ol; these regioisomers can be separated. Using MeI instead of BnCl will afford the corresponding mixture of methyl ethers, which can be separated.

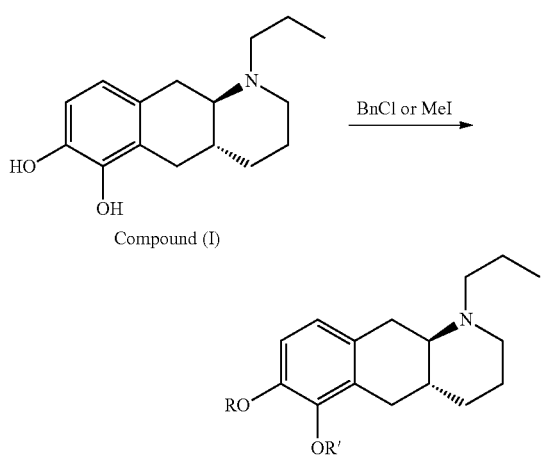

R = H, R' = Bn: (4aR,10aR)-6-(benzyloxy)-1-propyl-1,2,3,4,4a,5,10,10a-octahydrobenzo[g]quinolin-7-ol
R = Bn, R' = H: (4aR,10aR)-7-(benzyloxy)-1-propyl-1,2,3,4,4a,5,10,10a-octahydrobenzo[g]quinolin-6-ol
R = H, R' = Me: (4aR,10aR)-6-methoxy-1-propyl-1,2,3,4,4a,5,10,10a-octahydrobenzo[g]quinolin-7-ol
R = Me, R' = H: (4aR,10aR)-7-methoxy-1-propyl-1,2,3,4,4a,5,10,10a-octahydrobenzo[g]quinolin-6-ol Selective routes to (4aR,10aR)-7-(benzyloxy)-1-propyl-1,2,3,4,4a,5,10,10a-octahydrobenzo[g]quinolin-6-ol and (4aR,10aR)-7-methoxy-1-propyl-1,2,3,4,4a,5,10,10a-octahydrobenzo[g]quinolin-6-ol are provided herein.

INTERMEDIATES OF THE PRESENT INVENTION

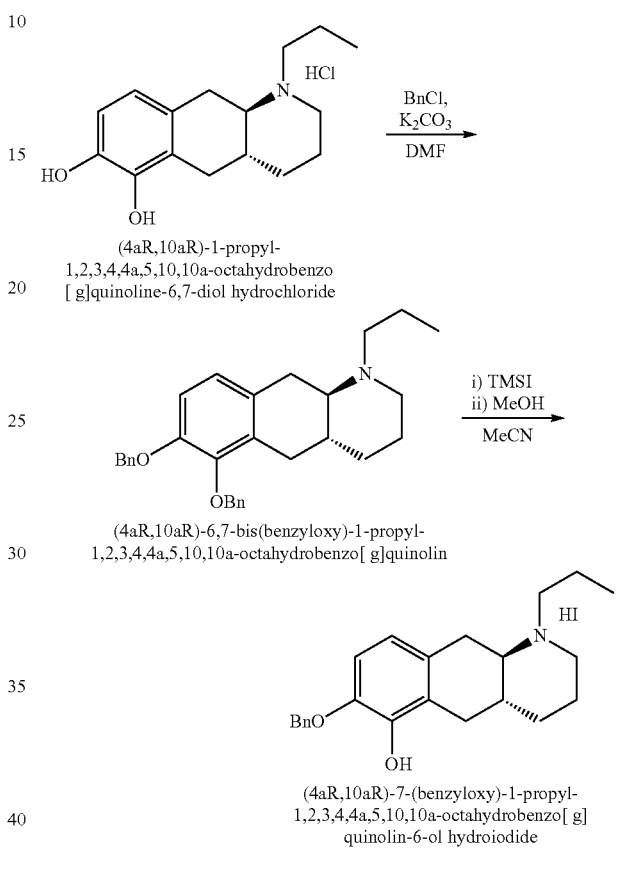

A1: (4aR,10aR)-6,7-bis(benzyloxy)-1-propyl-1,2,3,4,4a,5,10,10a-octahydrobenzo[g]quinoline The hydrochloride salt of Compound (I) (10.75 g) and K₂CO₃ (17.5 g) were added to a flask, which was degassed under vacuum and purged with N₂, before DMF (107 mL) and benzyl chloride (8.55 mL) were added and the mixture was stirred at room temperature for 18 hours, then at 100° C. for 5 hours, and at room temperature for 19 hours. K₂CO₃ (7.48 g) and benzyl chloride (6.29 mL) were added and the mixture was stirred at 100° C. for 5 hours. After cooling to room temperature, the mixture was partitioned between water (500 mL) and heptane (250 mL). The aqueous phase was washed with heptane (3×100 mL) and the combined organic phases were washed with brine (100 mL), dried over Na₂SO₄, filtered, and concentrated to afford the title compound (14.6 g).

A2-HI: (4aR,10aR)-7-(benzyloxy)-1-propyl-1,2,3,4,4a,5,10,10a-octahydrobenzo[q]quinolin-6-ol hydroiodide (4aR,10aR)-6,7-Bis(benzyloxy)-1-propyl-1,2,3,4,4a,5,10,10a-octahydrobenzo[g]quinoline) (11.9 g) was added to a flask, which was evacuated and purged with N₂, before MeCN (180 mL) was added. The mixture was stirred until homogeneous, before trimethylsilyl iodide (10.0 mL) was added and the mixture was stirred under N₂ at room temperature for 2 hours. MeOH (5.5 mL) was added and the mixture was stirred for 1 hour. Isopropyl acetate/heptane (10/150 mL) was added and the mixture was cooled to 0° C. and stirred for 1 hour. The solid was collected, washed with isopropyl acetate/heptane (3/47 mL), and dried to afford the title compound (7.6 g).

LCMS (method 550), retention time=0.55 minutes, [M+H]+=352.5 m/z.

$^1$H NMR (600 MHz, CDCl₃) δ 10.42 (bs, 1H), 7.43-7.33 (m, 4H), 7.26 (d, J=1.0 Hz, 1H), 6.78 (d, J=8.3 Hz, 1H), 6.58 (d, J=8.3 Hz, 1H), 5.72 (s, 1H), 5.08 (s, 2H), 3.71 (dd, J=11.70, 15.0 Hz, 1H), 3.58 (d, J=11.70, 1H), 3.25-3.11 (m, 4H), 2.94-2.86 (m, 1H), 2.77-2.57 (m, 2H), 2.26 (dd, J=11.70 Hz, 17.0 Hz 1H), 2.19 (d, J=13.80, 1H), 2.01-1.92 (m, 2H), 1.80-1.69 (m, 1H), 1.56-1.53 (m, 1H), 1.39 (qd, J=3.60 Hz, 13.30 Hz, 1H), 1.06 (t, J=7.2 Hz, 3H).

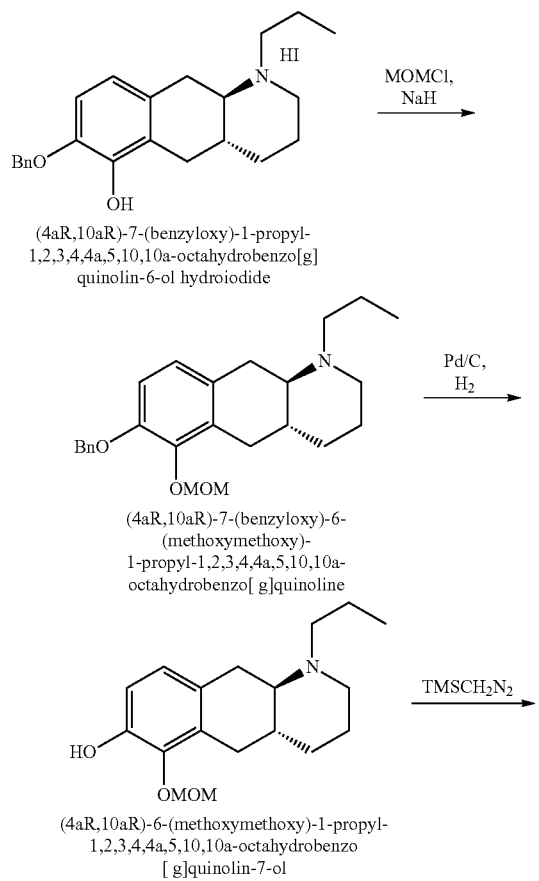

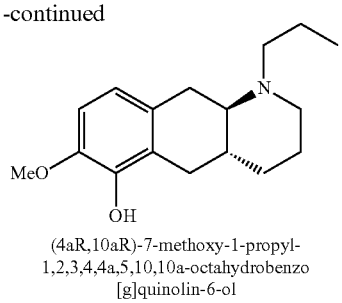

(4aR,10aR)-7-methoxy-1-propyl-1,2,3,4,4a,5,10,10a-octahydrobenzo[g]quinolin-6-ol

A3: (4aR,10aR)-7-(benzyloxy)-6-(methoxymethoxy)-1-propyl-1,2,3,4,4a,5,10,10a-octahydrobenzo[g]quinoline To a mixture of (4aR,10aR)-7-(benzyloxy)-1-propyl-1,2,3,4,4a,5,10,10a-octahydrobenzo[g]quinolin-6-ol hydroiodide (20 g) in DMF (400 mL) was added NaH (4.17 g, 60% dispersion) slowly at 0° C. under N₂. The mixture was stirred at 0° C. for 30 minutes before MOMCl (3.5 mL) was added drop-wise at 0° C. The mixture was stirred at room temperature for 1 hour before it was poured into water (400 mL) and stirred for 20 minutes and then extracted with EtOAc (300 mL×3). The combined organic layers were washed with brine (500 mL), dried over Na₂SO₄, filtered, and concentrated to afford the title compound (20 g).

A4: (4aR,10aR)-6-(methoxymethoxy)-1-propyl-1,2,3,4,4a,5,10,10a-octahydrobenzo[g]quinolin-7-ol To a solution of (4aR,10aR)-7-(benzyloxy)-6-(methoxymethoxy)-1-propyl-1,2,3,4,4a,5,10,10a-octahydrobenzo[g]quinoline (20 g) in MeOH (140 mL) was added Pd/C (10%, 30 g) under N₂. The suspension was degassed under vacuum and purged with H₂. The mixture was stirred under H₂ (50 psi) at room temperature for 12 hours, before the catalyst was filtered off. The filtrate was concentrated to afford the title compound (15.4 g).

A5: (4aR,10aR)-7-methoxy-6-(methoxymethoxy)-1-propyl-1,2,3,4,4a,5,10,10a-octahydrobenzo[g]quinoline To a solution of (4aR,10aR)-6-(methoxymethoxy)-1-propyl-1,2,3,4,4a,5,10,10a-octahydrobenzo[g]quinolin-7-ol (15 g) in MeOH (150 mL) was added drop-wise (trimethylsilyl)diazomethane (2M in hexane, 246 mL) at room temperature over 0.5 hour. The mixture was concentrated to afford the title compound (15 g).

A6: (4aR,10aR)-7-methoxy-1-propyl-1,2,3,4,4a,5,10,10a-octahydrobenzo[g]quinolin-6-ol A solution of (4aR,10aR)-7-methoxy-6-(methoxymethoxy)-1-propyl-1,2,3,4,4a,5,10,10a-octahydrobenzo[g]quinoline (15 g) in 4M HCl in MeOH (150 mL) was stirred at room temperature for 1 hour, before it was concentrated. The residue was dissolved in water (100 mL) and the aqueous layer was basified with NaHCO₃ to pH 7-8. The aqueous layer was extracted with EtOAc (100 mL and 50 mL). The combined organic layers were washed with brine (100 mL), dried over Na₂SO₄, filtered, and concentrated to afford the title compound (7 g).

LCMS (method 25), retention time=0.95 minutes, [M+H]⁺=276.1 m/z.

¹H NMR (400 MHz, CDCl₃) δ 6.70 (d, J=8.4 Hz, 1H), 6.62 (d, J=8.0 Hz, 1H), 5.71 (br s, 1H), 3.86 (s, 3H), 3.07-3.18 (m, 2H), 3.01 (dd, J=5.2, 17.6 Hz, 1H), 2.72-2.89 (m, 2H), 2.58-2.68 (m, 1H), 2.29-2.44 (m, 2H), 2.24 (dd, J=12.0, 17.6 Hz, 1H), 1.97 (d, J=13.2 Hz, 1H), 1.70-1.92 (m, 3H), 1.54-1.63 (m, 2H), 1.10-1.23 (m, 1H), 0.93 (t, J=7.2 Hz, 3H).

EXEMPLIFIED COMPOUNDS OF THE INVENTION

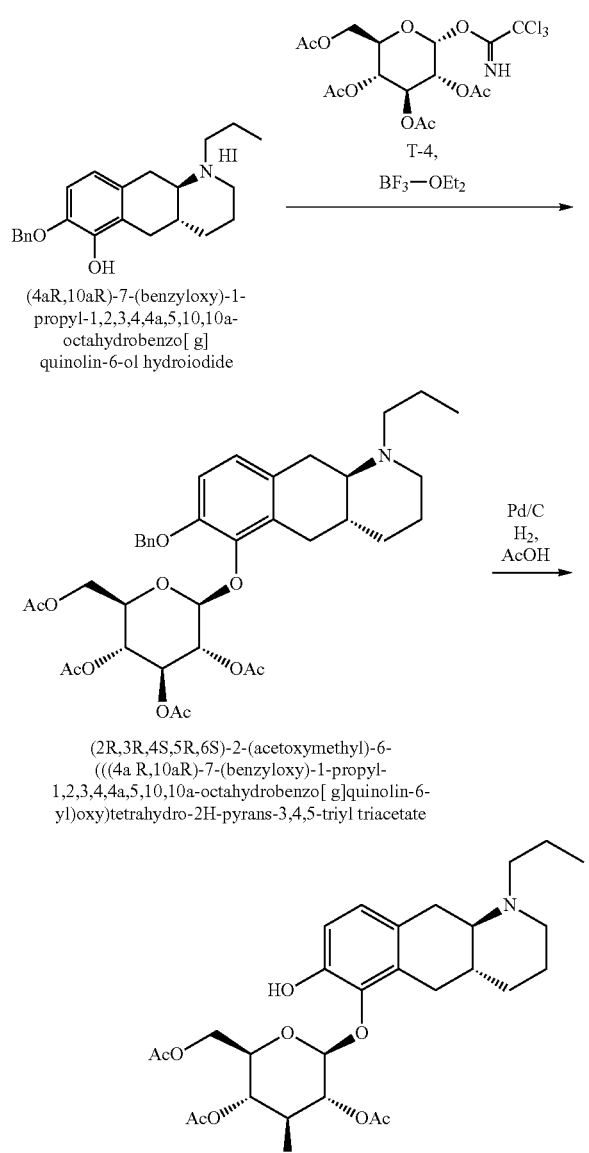

Compound (1): (2R,3R,4S,5R,6S)-2-(acetoxymethyl)-6-(((4aR,10aR)-7-(benzyloxy)-1-propyl-1,2,3,4,4a,5,10,10a-octahydrobenzo[g]quinolin-6-yl)oxy)tetrahydro-2H-pyran-3,4,5-triyl triacetate To a mixture of (2R,3R,4S,5R,6R)-2-(acetoxymethyl)-6-(2,2,2-trichloro-1-iminoethoxy)tetrahydro-2H-pyran-3,4,5-triyl triacetate (T-4; commercially available, 4.21 g), 4 Å MS (2 g) and (4aR,10aR)-7-(benzyloxy)-1-propyl-1,2,3,4,4a,5,10,10a-octahydrobenzo[g]quinolin-6-ol hydroiodide (2 g) in DCM (200 mL) was added a solution of BF₃—OEt₂ (2.2 mL) drop-wise at −20° C. over a period of 1 hour. The reaction mixture was allowed to warm to room temperature before it was partitioned between saturated aqueous NaHCO₃ (100 mL) and DCM (20 mL×2). The combined organic layers were dried over Na₂SO₄, filtered, and concentrated. The residue was purified by prep-HPLC (Xtimate C18 10 μm 250 mm×50 mm column; mobile phase: [water (0.04% NH₃H₂O)-ACN]; ACN %: 51%-72%, 29 min) to afford the title compound (0.8 g).

LCMS (method 10-90AB), retention time=0.96 minutes, [M+H]+=682.3 m/z.

QC-LC-MS (Method AB10), retention time=2.5 minutes, [M+H]+=682.3 m/z.

¹H NMR: (400 MHz DMSO) δ 7.53 (d, J=7.2 Hz, 2H), 7.32-7.40 (m, 3H), 6.87-6.96 (m, 2H), 5.29-5.37 (m, 2H), 5.09 (s, 2H), 4.94-5.04 (m, 2H), 4.09-4.13 (m, 1H), 3.96-4.01 (m, 2H), 3.14-3.22 (m, 5H), 2.85 (s, 1H), 2.12-2.30 (m, 2H), 2.03-2.14 (m, 1H), 1.96 (t, J=11.2 Hz, 9H), 1.70-1.80 (m, 2H), 1.40-1.69 (m, 7H), 1.06-1.23 (m, 1H), 0.87 (t, J=7.2 Hz, 3H).

Compound (2): (2R,3R,4S,5R,6S)-2-(acetoxymethyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate To a solution of (2R,3R,4S,5R,6S)-2-(acetoxymethyl)-6-(((4aR,10aR)-7-(benzyloxy)-1-propyl-1,2,3,4,4a,5,10,10a-octahydrobenzo[g]quinolin-6-yl)oxy)tetrahydro-2H-pyran-3,4,5-triyl triacetate (400 mg) in THF (20 mL) was added Pd/C (0.2 g, 50% (w/w)) and AcOH (0.067 mL) under N₂. The suspension was degassed under vacuum and purged with H₂. The mixture was stirred under H₂ (30 psi) at room temperature for 12 hours, before the catalyst was filtered off. The filtrate was concentrated and purified by prep-HPLC using a GX281 semi-preparative instrument (Phenomenex Luna C18 100×30 mm, 5 μm particles column operated at room temperature with 25 mL/min of a gradient of water+ 0.225% formic acid (A) and MeCN (B): 0-15 min 10-40% B; 15.1-17 min 100% B; 17.1-20 min 10% B) to afford the title compound (210 mg).

QC-LCMS (method AB01), retention time=2.66 minutes, [M+H]⁺=592.2 m/z.

¹H NMR (400 MHz, CDCl₃) δ 8.51 (s, 1H), 6.79 (q, J=8.4 Hz, 2H), 5.14-5.33 (m, 3H), 4.78 (d, J=8.0 Hz, 1H), 4.27 (dd, J=5.6, 12.8 Hz, 1H), 4.10 (dd, J=1.6, 12.0 Hz, 1H), 3.71-3.72 (m, 1H), 3.31 (d, J=11.6 Hz, 1H), 3.07-3.12 (m, 1H), 2.95-3.00 (m, 3H), 2.76-2.84 (m, 1H), 2.52-2.57 (m, 2H), 2.13-2.17 (m, 1H), 2.11 (s, 3H), 2.08 (s, 3H), 2.02 (s, 6H), 1.86-1.98 (m, 3H), 1.77-1.80 (m, 1H), 1.59-1.67 (m, 2H), 1.14-1.23 (m, 1H), 0.96 (t, J=7.6 Hz, 3H).

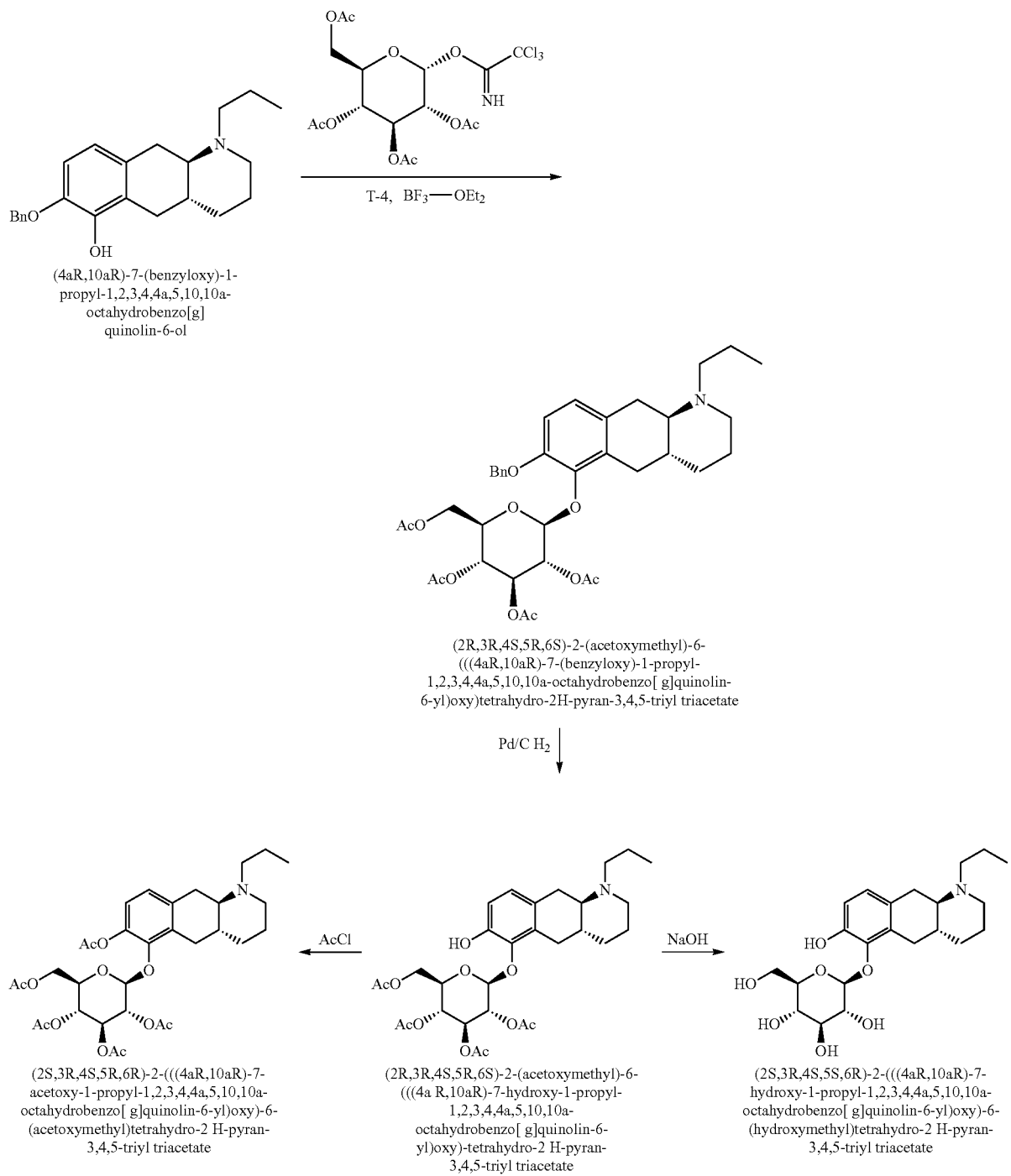

Compound (1): (2R,3R,4S,5R,6S)-2-(acetoxymethyl)-6-(((4aR,10aR)-7-(benzyloxy)-1-propyl-1,2,3,4,4a,5,10,10a-octahydrobenzo[g]quinolin-6-yl)oxy)tetrahydro-2H-pyran-3,4,5-triyl triacetate To a solution of (2R,3R,4S,5R,6R)-2-(acetoxymethyl)-6-(2,2,2-trichloro-1-iminoethoxy)tetrahydro-2H-pyran-3,4,5-triyl triacetate (T-4; commercially available, 6.31 g), 4 Å molecular sieves (3 g) and (4aR,10aR)-7-(benzyloxy)-1-propyl-1,2,3,4,4a,5,10,10a-octahydrobenzo[g]quinolin-6-ol (3 g) in DCM (300 mL) was added BF$_3$—OEt$_2$ (3.4 mL) drop-wise at −10° C. over a period of 1 hour. The reaction mixture was allowed to warm before it was partitioned between saturated aqueous NaHCO$_3$ (100 mL) and DCM (20 mL×2). The combined organic layers were dried over Na$_2$SO$_4$, filtered, and concentrated. The residue was purified by prep-HPLC using a Shimadzu LC20AP instrument (Xtimate C18 250×50 mm, 10 μm particles column operated at room temperature with 80 mL/min of a gradient of water +0.04% NH$_3$H$_2$O and MeCN (B): 0-28 min 51-72% B; 28.1-33 min 100% B; 33.1-37 min 51% B) to afford the title compound (2 g).

Compound (3): (2S,3R,4S,5R,6R)-2-(((4aR,10aR)-7-acetoxy-1-propyl-1,2,3,4,4a,5,10,10a-octahydrobenzo[g]quinolin-6-yl)oxy)-6-(acetoxymethyl)tetrahydro-2H-pyran-3,4,5-triyl triacetate To a mixture of (2R,3R,4S,5R,6S)-2-(acetoxymethyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate (1 g) and DIPEA (0.44 mL) in DCM (10 mL) was added acetyl chloride (0.15 mL) drop-wise at 0° C. under $N_2$. The mixture was stirred at room temperature for 2 hours before it was partitioned between water (20 mL) and DCM (10 mL×3). The combined organic layers were dried over $Na_2SO_4$, filtered, and concentrated. The residue was purified by prep-HPLC Shimadzhu LC20AP instrument (Phenomenex Luna C18 250×50 mm, 10 μm particles column operated at room temperature with 80 mL/min of a gradient of water+0.225% formic acid (A) and MeCN (B): 0-20 min 15-45% B; 20.1-25 min 100% B; 25.1-30 min 15% B) to afford the title compound (0.59 g).

QC-LCMS (method AB01), retention time=2.64 minutes, [M+H]=634.3 m/z.

$^1$H NMR (400 MHz, CDCl$_3$): δ 8.54 6.95 (d, J=8.4 Hz, 1H), 6.87 (d, J=8.4 Hz, 1H), 5.20-5.28 (m, 2H), 5.10-5.15 (m, 1H), 4.96 (d, J=7.4 Hz, 1H), 4.37 (dd, J=4.0, 12.4 Hz, 1H), 3.95 (d, J=8.4 Hz, 1H), 3.58-3.60 (m, 1H), 3.02-3.19 (m, 5H), 2.83 (s, 1H), 2.58 (s, 2H), 2.33 (s, 3H), 2.26-2.29 (m, 1H), 2.10 (s, 3H), 1.97-2.05 (m, 12H), 1.67-1.85 (m, 1H), 1.63-1.64 (m, 2H), 1.20-1.23 (m, 1H), 0.98 (t, J=7.6 Hz, 3H).

Compound (4): (2S,3R,4S,5S,6R)-2-(((4aR,10aR)-7-hydroxy-1-propyl-1,2,3,4,4a,5,10,10a-octahydrobenzo[g]quinolin-6-yl)oxy)-6-(hydroxymethyl)tetrahydro-2H-pyran-3,4,5-triol To a solution of NaOH (0.25 M, 47 mL) in MeOH (42 mL) and $H_2O$ (14 mL) was added (2R,3R,4S,5R,6S)-2-(acetoxymethyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate (1 g) at 0° C. under $N_2$, and the mixture was stirred at 0° C. for 1 hour. The mixture was concentrated. The residue was combined with the residues from two similar experiments. The combined materials were purified by prep-HPLC using a GX281 instrument (Phenomenex Luna C18 100×30 mm, 5 μm particles column operated at room temperature with 25 mL/min of a gradient of water+0.225% formic acid (A) and MeCN (B): 0-15 min 1-10% B; 15.1-17 min 100% B; 17.1-20 min 1% B) to afford the title compound (0.23 g).

$^1$H NMR (400 MHz, D$_2$O): δ 8.41 6.91 (d, J=8.4 Hz, 1H), 6.81 (d, J=8.4 Hz, 1H), 4.80 (d, J=7.8 Hz, 1H), 3.79-3.82 (m, 1H), 3.57-3.72 (m, 1H), 3.29-3.55 (m, 9H), 3.10-3.16 (m, 2H), 2.71-2.80 (m, 1H), 2.37 (dd, J=12.0, 16.0 Hz, 1H), 1.58-1.97 (m, 6H), 1.38-1.40 (m, 1H), 0.96 (t, J=7.2 Hz, 3H).

QC-LCMS (method AB01), 2etention time=1.95 minutes, [M+H]$^+$=424.2 m/z.

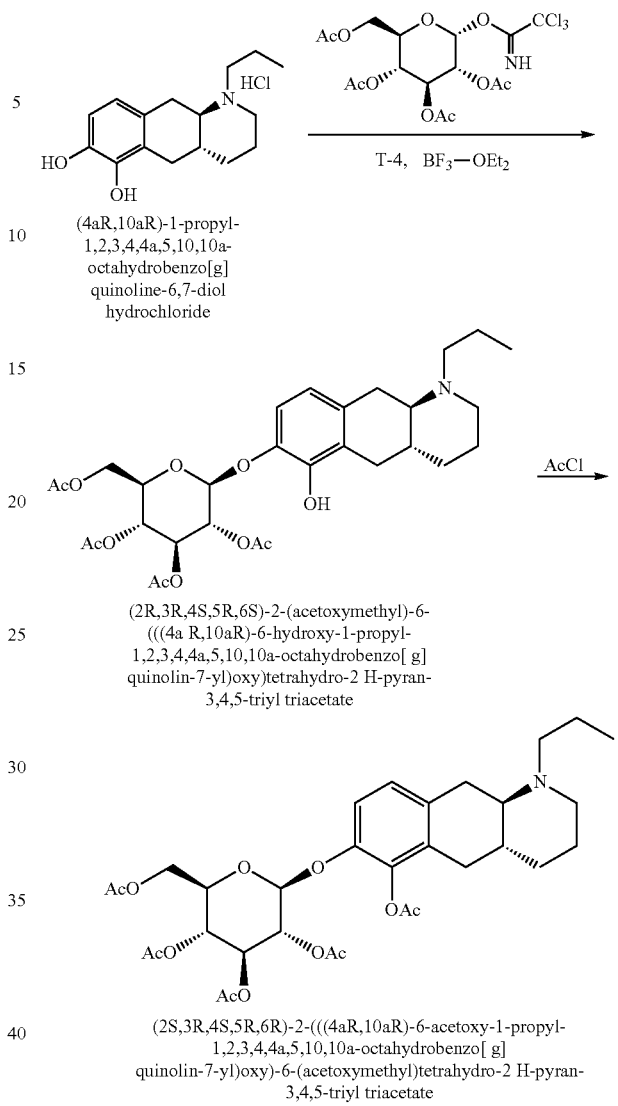

(4aR,10aR)-1-propyl-1,2,3,4,4a,5,10,10a-octahydrobenzo[g]quinoline-6,7-diol hydrochloride (2R,3R,4S,5R,6S)-2-(acetoxymethyl)-6-(((4a R,10aR)-6-hydroxy-1-propyl-1,2,3,4,4a,5,10,10a-octahydrobenzo[ g]quinolin-7-yl)oxy)tetrahydro-2 H-pyran-3,4,5-triyl triacetate (2S,3R,4S,5R,6R)-2-(((4aR,10aR)-6-acetoxy-1-propyl-1,2,3,4,4a,5,10,10a-octahydrobenzo[ g]quinolin-7-yl)oxy)-6-(acetoxymethyl)tetrahydro-2 H-pyran-3,4,5-triyl triacetate

Compound (5): (2R,3R,4S,5R,6S)-2-(acetoxymethyl)-6-(((4aR,10aR)-6-hydroxy-1-propyl-1,2,3,4,4a,5,10,10a-octahydrobenzo[g]quinolin-7-yl)oxy)tetrahydro-2H-pyran-3,4,5-triyl triacetate To a stirred solution of (4aR,10aR)-1-propyl-1,2,3,4,4a,5,10,10a-octahydrobenzo[g]quinoline-6,7-diol hydrochloride (1 g) in DCM (50 mL) was added BF$_3$—OEt$_2$ (0.83 mL) at room temperature. The reaction mixture was cooled to −20° C., before (2R,3R,4S,5R,6R)-2-(acetoxymethyl)-6-(2,2,2-trichloro-1-iminoethoxy)tetrahydro-2H-pyran-3,4,5-triyl triacetate (T-4; commercially available, 3.31 g) was added drop-wise as a solution in DCM (50 mL). The reaction was stirred at −20° C. for 1 hour and at room temperature for 3 hours. The mixture was partitioned between saturated aqueous NaHCO$_3$ (100 mL) and DCM (200 mL×2). The combined organic layers were washed with brine (200 mL), dried over Na$_2$SO$_4$, filtered, and concentrated. The residue was purified by prep-HPLC using a Shimadzu LC20AP instrument (Phenomenex Luna C18 250×50 mm, 10 μm particles column operated at room temperature with 80 mL/min of a gradient of water+0.225% formic acid (A) and MeCN (B): 0-20 min 10-40% B; 20.1-25 min 100% B; 25.1-30 min 10% B) to afford the title compound (0.5 g). This material was combined with a batch prepared in a similar manner (0.3 g). The combined material was purified by prep-HPLC using a GX281 instrument (Phenomenex Luna C18 100×30 mm, 5 μm particles column operated at room temperature with 25 mL/min of a gradient of water+ 0.225% formic acid (A) and MeCN (B): 0-15 min 1-30% B; 15.1-17 min 100% B; 17.1-20 min 1% B) to afford the title compound (0.20 g).

$^1$H NMR (400 MHz, DMSO-$d_6$) δ 8.13 (br s, 1H), 6.82 (d, J=8.4 Hz, 1H), 6.56 (d, J=8.4 Hz, 1H), 5.32-5.35 (m, 2H), 4.95-5.07 (m, 2H), 4.14-4.21 (m, 2H), 4.03 (d, J=10.4 Hz, 1H), 3.10 (dd, J=4.4, 16.4, Hz, 1H), 2.92 (d, J=11.2 Hz, 1H), 2.81 (dd, J=17.6, 5.2 Hz, 1H), 2.66-2.76 (m, 1H), 2.36-2.46 (m, 1H), 2.25-2.35 (m, 1H), 2.11-2.21 (m, 1H), 2.03-2.10 (m, 2H), 1.98-2.03 (m, 9H), 1.94-1.97 (m, 1H), 1.95 (s, 3H), 1.83 (d, J=10.8 Hz, 1H), 1.57-1.67 (m, 1H), 1.54 (d, J=12.8 Hz, 1H), 1.36-1.50 (m, 2H), 1.01-1.14 (m, 1H), 0.85 (t, J=7.2 Hz, 3H).

QC-LCMS: (Method AB01), retention time=2.66 minutes, [M+H]+=592.3 m/z.

Compound (6): (2S,3R,4S,5R,6R)-2-(((4aR,10aR)-6-acetoxy-1-propyl-1,2,3,4,4a,5,10,10a-octahydrobenzo[g]quinolin-7-yl)oxy)-6-(acetoxymethyl)tetrahydro-2H-pyran-3,4,5-triyl triacetate To a stirred solution of (2R,3R,4S,5R,6S)-2-(acetoxymethyl)-6-(((4aR,10aR)-6-hydroxy-1-propyl-1,2,3,4,4a,5,10,10a-octahydrobenzo[g]quinolin-7-yl)oxy)tetrahydro-2H-pyran-3,4,5-triyl triacetate (0.8 g) in DCM (8 mL) was added DIPEA (0.47 mL) and acetyl chloride (0.15 mL) at 0° C. under $N_2$. The reaction mixture was stirred at room temperature for 1 hour, before it was partitioned between $H_2O$ (50 mL) and DCM (100 mL×2). The combined organic layers were washed with brine (100 mL), dried over $Na_2SO_4$, filtered, and concentrated. The residue was purified by prep-HPLC using a GX281 instrument (Phenomenex Luna C18 100×30 mm, 5 μm particles column operated at room temperature with 25 mL/min of a gradient of water+ 0.225% formic acid (A) and MeCN (B): 0-15 min 5-45% B; 15.1-17 min 100% B; 17.1-20 min 5% B) to afford the title compound (0.25 g).

$^1$H NMR (400 MHz, DMSO-$d_6$) δ 7.03 (d, J=8.8 Hz, 1H), 6.92 (d, J=8.8 Hz, 1H), 5.38-5.45 (m, 2H), 4.98-5.07 (m, 2H), 4.18-4.22 (m, 1H), 4.10 (d, J=2.4 Hz, 1H), 4.06 (d, J=2.0 Hz, 1H), 3.19 (d, J=16.0 Hz, 1H), 2.94 (d, J=1.6 Hz, 1H), 2.67-2.69 (m, 2H), 2.34 (d, J=2.0 Hz, 2H), 2.20 (s, 3H), 2.03-2.15 (m, 2H), 1.97-2.03 (m, 13H), 1.82 (d, J=10.4 Hz, 1H), 1.44-1.61 (m, 5H), 0.98-1.10 (m, 1H), 0.86 (t, J=7.2 Hz, 3H).

QC-LCMS (method DELIVER-K), retention time=1.58 minutes, [M+H]+=634.2 m/z.

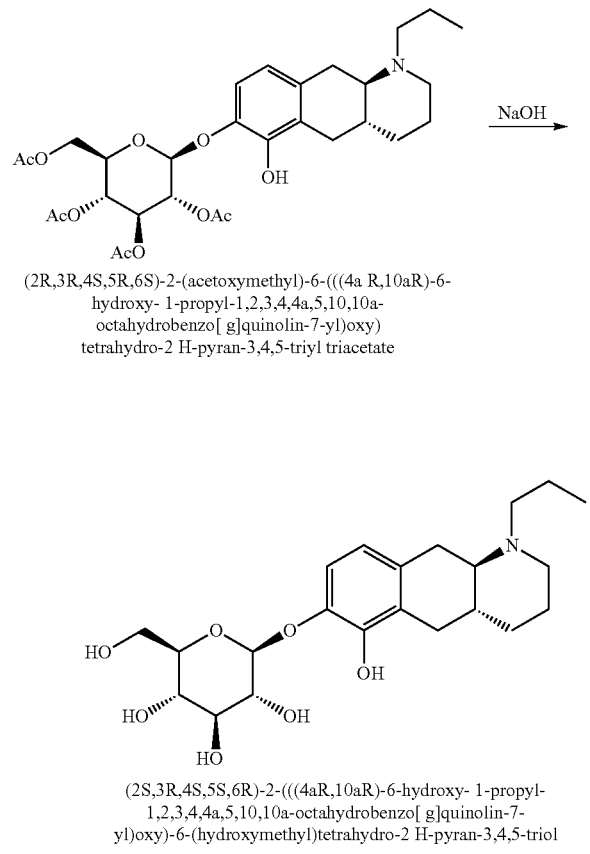

(2R,3R,4S,5R,6S)-2-(acetoxymethyl)-6-(((4a R,10aR)-6-hydroxy-1-propyl-1,2,3,4,4a,5,10,10a-octahydrobenzo[g]quinolin-7-yl)oxy)tetrahydro-2 H-pyran-3,4,5-triyl triacetate (2S,3R,4S,5S,6R)-2-(((4aR,10aR)-6-hydroxy-1-propyl-1,2,3,4,4a,5,10,10a-octahydrobenzo[g]quinolin-7-yl)oxy)-6-(hydroxymethyl)tetrahydro-2 H-pyran-3,4,5-triol Compound (7): (2S,3R,4S,5S,6R)-2-(((4aR,10aR)-6-hydroxy-1-propyl-1,2,3,4,4a,5,10,10a-octahydrobenzo[g]quinolin-7-yl)oxy)-6-(hydroxymethyl)tetrahydro-2H-pyran-3,4,5-triol To a stirred solution of (2R,3R,4S,5R,6S)-2-(acetoxymethyl)-6-(((4aR,10aR)-6-hydroxy-1-propyl-1,2,3,4,4a,5,10,10a-octahydrobenzo[g]quinolin-7-yl)oxy)tetrahydro-2H-pyran-3,4,5-triyl triacetate (0.8 g) in MeOH (24 mL) and water (8 mL) was added NaOH (270 mg) at 0° C. The reaction mixture was stirred 0° C. for 3 hours, before it was concentrated. The residue was purified by prep-HPLC using a Shimadzhu LC20AP instrument (Phenomenex Luna C18 250×50 mm, 10 μm particles column operated at room temperature with 80 mL/min of a gradient of water+0.225% formic acid (A) and MeCN (B): 0-20 min 1-25% B; 20.1-25 min 100% B; 25.1-30 min 1% B) to afford the title compound (0.20 g).

$^1$H NMR: (400 MHz, DMSO-$d_6$) δ 8.21 (s, 1H), 6.91 (d, J=8.4 Hz, 1H), 6.50 (d, J=8.4 Hz, 1H), 4.48 (d, J=7.2 Hz, 1H), 3.35-4.0 (m, 5H), 3.20-3.30 (m, 4H), 3.06-3.18 (m, 3H), 3.00 (d, J=10.4 Hz, 1H), 2.72-2.89 (m, 2H), 2.36-2.47 (m, 1H), 2.17-2.34 (m, 2H), 2.07 (dd, J=11.6, 17.2 Hz, 1H), 1.85 (d, J=11.6 Hz, 1H), 1.39-1.70 (m, 5H), 1.04-1.17 (m, 1H), 0.86 (t, J=7.2 Hz, 3H).

QC-LCMS (method AB01), retention time=1.87 minutes, [M+H]+=424.2 m/z.

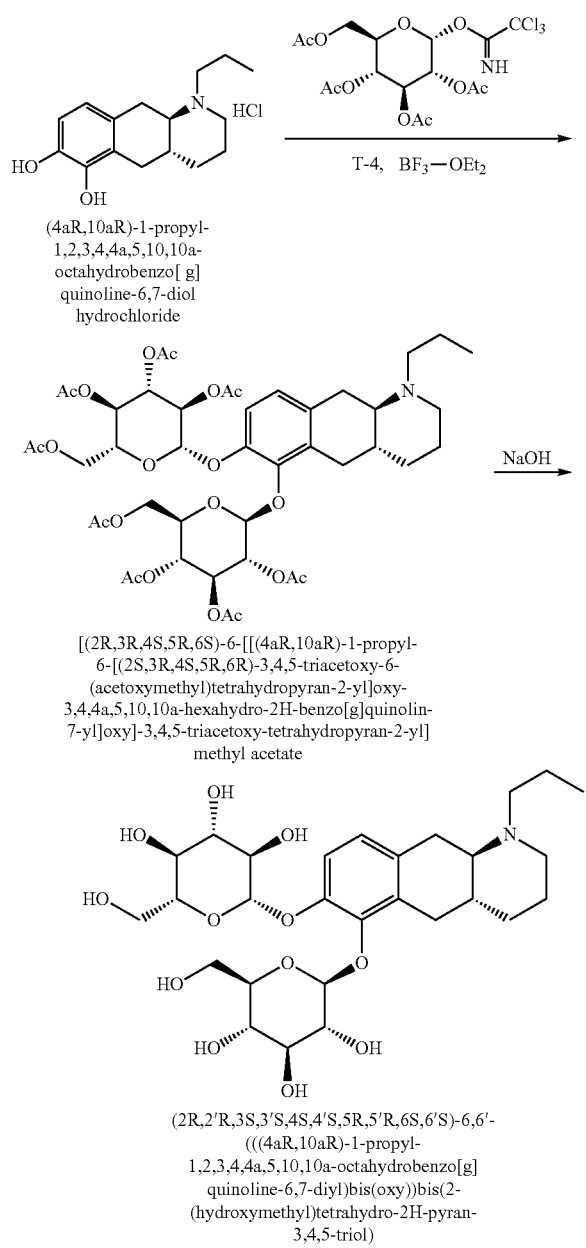

Compound (8): [(2R,3R,4S,5R,6S)-6-[[(4aR,10aR)-1-propyl-6-[(2S,3R,4S,5R,6R)-3,4,5-triacetoxy-6-(acetoxymethyl)tetrahydropyran-2-yl]oxy-3,4,4a,5,10,10a-hexahydro-2H-benzo[g]quinolin-7-yl]oxy]-3,4,5-triacetoxy-tetrahydropyran-2-yl]methyl acetate To a stirred solution of (4aR,10aR)-1-propyl-1,2,3,4,4a,5,10,10a-octahydrobenzo[g]quinoline-6,7-diol hydrochloride (2 g) in DCM (100 mL) was added (2R,3R,4S,5R,6R)-2-(acetoxymethyl)-6-(2,2,2-trichloro-1-iminoethoxy)tetrahydro-2H-pyran-3,4,5-triyl triacetate (T-4; commercially available, 13.2 g). The mixture was cooled to −20° C., before $BF_3$—$OEt_2$ (3.3 mL) was added drop-wise. The reaction was stirred at −20° C. for 1 hour and at room temperature for 2 hours. The mixture was concentrated. The residue was purified by prep-HPLC using a Agela FI-H600G instrument (Agela Innoval ods-2 250×80 mm, 10 μm particles column operated at room temperature with 160 mL/min of a gradient of water+0.225% formic acid (A) and MeCN (B): 0-20 min 22-52% B; 20.1-25 min 100% B; 25.1-30 min 22% B) to afford the title compound (3.0 g). 0.5 g of this material was re-purified by prep-HPLC using a GX281 instrument (Waters Atlantis T3 150×30 mm, 5 μm particles column operated at room temperature with 25 mL/min of a gradient of water+0.225% formic acid (A) and MeCN (B): 0-13 min 15-55% B; 13.1-15 min 100% B; 15.1-18 min 15% B) to afford the title compound (0.25 g).

$^1$H NMR (400 MHz, DMSO-$d_6$) δ 6.92-6.99 (m, 2H), 5.69 (d, J=7.6 Hz, 1H), 5.43-5.49 (m, 2H), 5.20-5.30 (m, 1H), 4.99-5.14 (m, 4H), 4.28 (dd, J=4.8, 12.8, Hz, 1H), 4.12-4.15 (m, 2H), 4.01-4.04 (m, 2H), 3.70-3.82 (m, 1H), 3.15 (dd, J=4.8, 16.4 Hz, 2H), 2.89-3.03 (m, 2H), 2.65-2.77 (m, 1H), 2.43 (dd, J=10.8, 16.0 Hz, 1H), 2.25-2.36 (m, 1H), 2.10-2.23 (m, 1H), 2.05 (s, 3H), 2.04 (s, 3H), 2.02 (s, 3H), 2.01 (s, 3H), 1.96-2.00 (m, 9H), 1.92 (s, 3H), 1.74-1.87 (m, 1H), 1.32-1.70 (m, 6H), 0.99-1.16 (m, 1H), 0.86 (t, J=7.2 Hz, 3H).

QC-LCMS (method AB25—MS1500), retention time=2.05 minutes, [M+H]+=922.3 m/z.

Compound (9): (2R,2'R,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(2-(hydroxymethyl)tetrahydro-2H-pyran-3,4,5-triol)

To a solution of [(2R,3R,4S,5R,6S)-6-[[(4aR,10aR)-1-propyl-6-[(2S,3R,4S,5R,6R)-3,4,5-triacetoxy-6-(acetoxymethyl)tetrahydropyran-2-yl]oxy-3,4,4a,5,10,10a-hexahydro-2H-benzo[g]quinolin-7-yl]oxy]-3,4,5-triacetoxy-tetrahydropyran-2-yl]methyl acetate (1.0 g) in MeOH (30 mL) and $H_2O$ (10 mL) was added NaOH (434 mg) at 0° C. The mixture was stirred at 0° C. for 3 hours, before it was concentrated. The residue was purified by prep-HPLC using a Shimadzhu LC20AP instrument (Phenomenex Luna C18 250×50 mm, 10 μm particles column operated at room temperature with 80 mL/min of a gradient of water+0.225% formic acid (A) and MeCN (B): 0-20 min 1-20% B; 20.1-25 min 100% B; 25.1-30 min 1% B) to afford the title compound (0.20 g).

$^1$H NMR (400 MHz, DMSO-$d_6$) δ 7.03 (d, J=8.4 Hz, 1H), 6.82 (d, J=8.4 Hz, 1H), 4.87 (d, J=7.6 Hz, 1H), 4.60 (d, J=7.6 Hz, 1H), 3.72 (d, J=10.0 Hz, 1H), 3.60 (d, J=10.0 Hz, 1H), 3.39-3.51 (m, 2H), 3.19-3.33 (m, 6H), 3.08-3.18 (m, 3H), 2.99-3.06 (m, 1H), 2.94 (d, J=10.0 Hz, 1H), 2.65-2.77 (m, 1H), 2.43 (m, 1H), 2.27-2.37 (m, 1H), 2.00-2.21 (m, 3H), 1.82 (d, J=12.0 Hz, 1H), 1.35-1.67 (m, 5H), 0.97-1.11 (m, 1H), 0.85 (t, J=7.2 Hz, 3H).

QC-LCMS (method AB00), retention time=2.18 minutes, [M+H]+=586.3 m/z.

IN VITRO AND IN VIVO CHARACTERIZATION OF COMPOUNDS OF THE INVENTION

Example 1: Conversion of Compounds in Human Plasma and Hepatocytes

Example 1a: Conversion of Compounds of the Invention in Human Plasma

Frozen human plasma was thawed and then centrifuged at 3200×g for 5 minutes to remove debris. The pH value of the supernatant was then measured and adjusted to 7.4±0.1 by adding 1% phosphoric acid or 1 N sodium hydroxide. 2 μL of dosing solution (50 μM for test compounds and 100 μM for positive control (propantheline bromide)) was mixed with 98 μL of blank plasma to achieve 1 μM test compound and 2 μM positive control of final concentration. The mixture was incubated, and samples were withdrawn from the incubations at the pre-determined time points of 0, 0.5, 1, 2, 4 and 6 hours (in duplicate) at 37° C. in water bath. At each corresponding time point 10 μL inhibitor and 20 μL ascorbic acid and 2 μL formic acid (20%) are added, and then added 400 μL of "stop solution" (200 ng/mL tolbutamide plus 200 ng/mL labetalol in 50% ACN/MeOH) to precipitate protein. The substance was mixed thoroughly and thereafter centrifuged at 4,000 rpm for 20 minutes. Then an aliquot of supernatant (50 μL) was transferred from each well to a sample plate and mixed with 100 μL ultrapure water. The plate was shaked at 800 rpm for about 10 minutes before submitting to LC-MS/MS analysis.

Example 1b: Conversion of Compounds of the Invention in Human Hepatocytes

Incubations were conducted in 96-well plates at 1 μM compound concentration in duplicate. The hepatocyte cell concentration was 0.5×106 cells/mL used for final incubation at 37° C. in an incubator of 5% $CO_2$ 95% relative humidity. The medium control samples were included at 0 and 60 minutes in the absence of cells. The total organic concentration was 1% (DMSO 0.1%) in the final incubation. The controls, (7-ethoxycoumarin and 7-hydroxycoumarin) was incubated parallel at 3 μM. 2 μL of dosing solution (50 μM for test compounds and 100 μM for positive control) was mixed with 98 μL of 100 mM PBS to achieve 1 μM test compound and 2 μM positive control of final concentration. The mixture was incubated, and samples were withdrawn from the incubations at pre-determined time points of 0, 0.5, 1, 2, 4 and 6 hour (in duplicate) at 37° C. in water bath. To each sample, 10 μL inhibitor and 20 μL ascorbic acid and 2 μL formic acid (20%) were added followed by 400 μL of stop solution (200 ng/mL tolbutamide plus 200 ng/mL labetalol in 50% ACN/MeOH). The substance was mixed thoroughly and thereafter centrifuged at 4,000 rpm for 20 minutes. An aliquot of supernatant (50 μL) from each well were transferred to a sample plate and mixed with 100 μL ultrapure water. The plate was shaked at 800 rpm for about 10 minutes before submitting to LC-MS/MS analysis.

Instrumentation Used for Analysis of Plasma and Hepatocyte Incubation Samples

Mass spectrometer (LC-MS/MS) Shimadzu LC 20-AD Shimadzu UHPLC API 4000. Analytical column ACQUITY UPLC® BEH Phenyl 1.7 μm 2.1×50 mm. Mobile phase A: 0.1% Formic Acid in Water. Mobile phase B: 0.1% Formic Acid in Acetonitrile. Gradient run from 95/5% to 5/95 in 2.0 minutes. Flow rate 0.7 mL/min. MRM monitoring (multiple reaction monitoring) of test item and the added analytical standards (Labetalol or Tolbutamide).

Example 2: 5-HT2B Agonist Activity and Binding Assay

5-HT2B agonist activity assay

Evaluation of the agonist activity of compounds (I), (Ia) and (Ib) at the human 5-HT2B receptor was performed by Eurofins/Cerep (France) measuring the compound effects on inositol monophosphate (IP1) production using the HTRF detection method. Briefly, the human 5-HT2B receptor was expressed in transfected CHO cells. The cells were suspended in a buffer containing 10 mM Hepes/NaOH (pH 7.4), 4.2 mM KCl, 146 mM NaCl, 1 mM $CaCl_2$, 0.5 mM MgCl2, 5.5 mM glucose and 50 mM LiCl, then distributed in microplates at a density of 4100 cells/well and incubated for 30 minutes at 37° C. in the presence of buffer (basal control), test compound or reference agonist. For stimulated control measurement, separate assay wells contained 1 μM 5-HT. Following incubation, the cells were lysed and the fluorescence acceptor (fluorophen D2-labeled IP1) and fluorescence donor (anti-IP1 antibody labeled with europium cryptate) were added. After 60 minutes at room temperature, the fluorescence transfer was measured at lambda(Ex) 337 nm and lambda(Em) 620 and 665 nm using a microplate reader (Rubystar, BMG). The IP1 concentration was determined by dividing the signal measured at 665 nm by that measured at 620 nm (ratio). The results were expressed as a percent of the control response to 1 μM 5-HT. The standard reference agonist was 5-HT, which was tested in each experiment at several concentrations to generate a concentration-response curve from which its $EC_{50}$ value is calculated as described above for dopamine functional assays.

5-HT2B Binding Assay

Evaluation of the affinity of compounds for the human 5-HT2B receptor was determined in a radioligand binding assay at Eurofins/Cerep (France). Membrane homogenates prepared from CHO cells expressing the human 5HT2B receptor were incubated for 60 minutes at room temperature with 0.2 nM [1251](±)DOI (1-(4-iodo-2, 5-dimethoxyphenyl)propan-2-amine) in the absence or presence of the test compound in a buffer containing 50 mM Tris-HCl (pH 7.4), 5 mM $MgCl_2$, 10 μM pargyline and 0.1% ascorbic acid. Nonspecific binding is determined in the presence of 1 μM (±)DOI. Following incubation, the samples were filtered rapidly under vacuum through glass fiber filters (GF/B, Packard) presoaked with 0.3% polyethyleneimine (PEI) and rinsed several times with ice-cold 50 mM Tris-HCl using a 96-sample cell harvester (Unifilter, Packard). The filters were dried and counted for radioactivity in a scintillation counter (Topcount, Packard) using a scintillation cocktail (Microscint 0, Packard). The results are expressed as a percent inhibition of the control radioligand specific binding. The standard reference compound was (±)DOI, which was tested in each experiment at several concentrations to obtain a competition curve from which its $IC_{50}$ is calculated.

TABLE 3

In vitro activities for compounds of the invention obtained according to Example 2

| | Compound | 5-HT2B $EC_{50}$ (nM)/Emax |
|---|---|---|
| Parent compound | (I) | 2900 nM/50% |
| State of the art prodrugs | (Ia) | >6000 nM, 58% @ 30 uM |
| | (Ib) | 3.8 nM/79% |
| | (Ic) | −5% @ 10 μM |
| Compounds of the invention | Compound (2) | −6% @ 10 μM |
| | Compound (3) | 18% @ 10 μM |
| | Compound (4) | 0% @ 10 μM |
| | Compound (5) | 9% @ 10 μM |
| | Compound (6) | −5% @ 10 μM |
| | Compound (7) | 7% @ 10 μM |
| | Compound (8) | −12% @ 10 μM |
| | Compound (9) | −5% @ 10 μM |
| | A2 | 30% @ 10 μM |
| | A6 | 24% @ 10 μM |

* indicate binding affinity (% inhibition of control, specific binding at concentration indicated)

Example 3: PK Experiments in Rats

For all the experiments, blood samples of approximately 0.68 mL were drawn from the tail or sublingual vein and put into K$_3$EDTA tubes that had been pre-cooled and prepared with stabilizing solution consisting of 80 µL ascorbic acid and 40 µL 100 mM D-saccharic acid 1,4 lactone in water. The tubes were inverted gently 6-8 times to ensure thorough mixing and then placed in wet ice. The collecting tube was placed in wet ice for up to 30 minutes until centrifugation. Once removed from the wet ice the centrifugation was initiated immediately. Immediately after end of centrifugation the samples were returned to wet ice. Three sub-samples of 130 µL plasma were transferred to each of three appropriately labelled cryo tubes containing 6.5 µL pre-cooled formic acid (20%) (the tubes were pre-spiked and stored refrigerated prior to use). The tube lid was immediately replaced and the plasma solution was thoroughly mixed by inverting gently 6-8 times. The samples were stored frozen at nominally −70° C. within 60 minutes after sampling. Centrifugation conditions at 3000 G for 10 minutes at 4° C. Plasma was placed on water-ice following collection. Final storage at approximately −70° C.

Plasma samples were analyzed by solid phase extraction or direct protein precipitation followed by UPLC-MS/MS. MS detection using electrospray in the positive ion mode with monitoring of specific mass-to-charge transitions for compound (I) using internal standards for correcting the response. The concentration-time data was analyzed, using standard software using appropriate noncompartmental techniques to obtain estimates of the derived PK parameters.
Instrumentation Used for Analysis of Compound (I) from Dosing Compound (Ia):

Mass spectrometer (LC-MS/MS) Waters Acquity-Sciex API 5000. Analytical column Waters BEH UPLC Phenyl 100×2.1 mm column, 1.7 µm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring (multiple reaction monitoring) of test item and the added analytical standards.

Dosing and blood sampling: Han Wistar rats were supplied by Charles River Laboratories, Sulzfeld, Germany. An artificial, automatically controlled, light and dark cycle of 12 hours was maintained. The rats received a standard laboratory diet from Brogaarden (Altromin 1324 pellets). The rats had unrestricted access to the diet. During the study (a 4-week toxicity study) the rats received once daily doses of (Ia) orally by gavage. From rats given 300 µg/kg (Ia), blood samples) from 3 male satellite animals were collected on the following time points at Day 29: 0.5, 1, 2, 4, 6, 8, 12 and 24 hours after dosing.
Instrumentation Used for Analysis of Compound (I) from Dosing of Compound (Ib):

Mass spectrometer (LC-MS/MS) Waters Acquity-Sciex API 5000. Analytical column Waters BEH UPLC Phenyl 100×2.1 mm column, 1.7 µm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring of test item and the added analytical standards.

Dosing and blood sampling: Han Wistar rats were supplied by Charles River Laboratories, UK. An artificial, automatically controlled, light and dark cycle of 12 hours was maintained. The rats received a standard laboratory diet (Teklad 2014C Diet.). The rats had unrestricted access to the diet. During the study (a 26-week toxicity study) the rats received once daily doses of (Ib) orally by gavage. From rats given 300 ag/kg (Ib), blood samples from 3 male satellite animals were collected on the following time points at day 182: 0.5, 1, 2, 4, 8 and 24 hours after dosing.
Instrumentation Used for Analysis of Compound (I) from Dosing of Compounds (Ic), Compound 7, Compound (4), Compound (9), A6 and A2

Mass spectrometer (LC-MS/MS) Waters Acquity—Waters Xevo TQ-S. Analytical column Acquity BEH C18 100×2.1 mm, 1.7 µm. Mobile phase A: 20 mM NH$_4$—Formate+0.2% formic acid. Mobile phase B: Acetonitrile+0.2% formic acid. Gradient run from 95/5% to 5/95% in 11.0 minutes. Flow rate 0.3 mL/min. MRM monitoring of test item and the added analytical standards.

Dosing and blood sampling: Han Wistar rats were supplied by Envigo, UK. An artificial, automatically controlled, light and dark cycle of 12 hours was maintained. The rats received a standard laboratory diet Teklad 2014C. The rats had unrestricted access to the diet. Male Han Wistar rats were dosed a single oral gavage administration of test compound orally by gavage. Rats were given 494 ag/kg (Ic), 487 ag/kg compound (7), 487 ag/kg Compound (4), 674 ag/kg compound (9), 359 ag/kg A6 and 551 ag/kg A2. Blood samples from 3 male animals were collected on the following time points at Day 1: 0.125, 0.25, 0.5, 1, 2, 4, 8, and 24 hours after dosing.

TABLE 4

PK parameters for (4aR,10aR)-1-Propyl-1,2,3,4,4a,5,10,10a-octahydro-benzo[g]quinoline-6,7-diol (compound (I)) after oral dosing of 0.300 mg/kg (Ia), 0.300 mg/kg (Ib), 494 µg/kg (Ic), 487 µg/kg compound (7), 487 µg/kg compound (4), 674 µg/kg compound (9), 359 µg/kg A6 and 551 µg/kg A2 to Wistar rats according to Example 3

|  | compound | $T_{max}$ (h) | $C_{max}$ (pg/mL) | AUC$_{0-24}$ (pg*h/mL) | Exposure at 24 h (pg/mL) |
|---|---|---|---|---|---|
| Prior art prodrugs | (Ia) | 1.0 | 3160 | 13600 | 48 ± 26 |
|  | (Ib) | 1.0 | 4990 | 31000 | 147 ± 28 |
|  | (Ic) | 1.0 | 14 | 104 | N/A |
| Compounds of the invention | Compound (4) | 2 | 970 | 19000 | 859 ± 133 |
|  | Compound (7) | 2 | 616 | 7100 | 198 ± 43.7 |
|  | Compound (9) | 8 | 525 | 8330 | 233 ± 50.7 |
|  | A2 | 24 | 380 | 5590 | 380 ± 230 |
|  | A6 | 8 | 77 | 1380 | 39 ± 10 |

The invention claimed is:
1. A compound according to formula (Id)

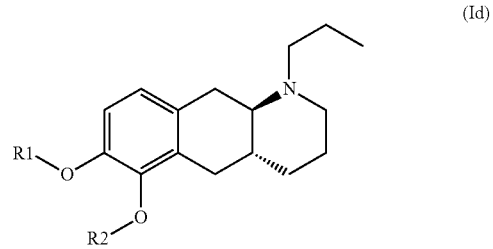

(Id)

wherein R1 and R2 are defined according to a) to c) below:
  a) R1 is selected from H, C$_1$-C$_6$ alkyl, benzyl and linear-C(O) C$_1$-C$_6$ alkyl and R2 is substituent (i) below; or b) R1 is substituent (i) below and R2 is selected from H, C$_1$-C$_6$ alkyl, benzyl and linear-C(O) C$_1$-C$_6$ alkyl; or c) R1 and R2 are both represented by substituent (i) below

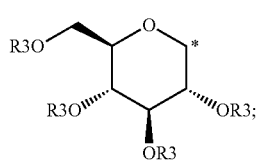

(i)

and
wherein R3 is selected from H and —C(O) C$_1$-C$_6$ alkyl; and
wherein * indicates the attachment point; and
wherein the carbon atom at the attachment point on substituent (i) is in the S-configuration;
with the proviso that when one of R1 or R2 is substituent (i) and R3 is H then the other of R1 or R2 cannot be linear-C(O) C$_1$-C$_6$ alkyl;
or a pharmaceutically acceptable salt thereof.

2. The compound or pharmaceutically acceptable salt thereof according to claim 1, wherein
R1 is selected from H, C$_1$-C$_6$ alkyl, benzyl and linear-C(O) C$_1$-C$_6$ alkyl; and R2 is substituent (i).

3. The compound or pharmaceutically acceptable salt thereof according to claim 1, wherein
R1 is substituent (i); and R2 is selected from H, C$_1$-C$_6$ alkyl, benzyl and linear-C(O) C$_1$-C$_6$ alkyl.

4. The compound or pharmaceutically acceptable salt thereof according to claim 1, wherein
R1 and R2 are both represented by substituent (i).

5. The compound or pharmaceutically acceptable salt thereof according to claim 1, wherein R1 or R2 is —C(O)methyl.

6. The compound or pharmaceutically acceptable salt thereof according to claim 1, wherein R3 is —C(O)methyl.

7. The compound or pharmaceutically acceptable salt thereof according to claim 1, wherein R3 is H.

8. The compound or pharmaceutically acceptable salt thereof according to claim 1, wherein one of R1 and R2 is H; and wherein one of R1 and R2 is substituent (i); and wherein R3 is H.

9. The compound according to claim 1, wherein the compound is selected from the group consisting of:
  (2R,3R,4S,5R,6S)-2-(acetoxymethyl)-6-(((4aR,10aR)-7-(benzyloxy)-1-propyl-1,2,3,4,4a,5,10,10a-octahydrobenzo [g]quinolin-6-yl)oxy) tetrahydro-2H-pyran-3,4,5-triyl triacetate;
  (2R,3R,4S,5R,6S)-2-(acetoxymethyl)-6-(((4aR,10aR)-7-hydroxy-1-propyl-1,2,3,4,4a,5,10,10a-octahydrobenzo [g]quinolin-6-yl)oxy) tetrahydro-2H-pyran-3,4,5-triyl triacetate;
  (2S,3R,4S,5R,6R)-2-(((4aR,10aR)-7-acetoxy-1-propyl-1,2,3,4,4a,5,10,10a-octahydrobenzo [g]quinolin-6-yl) oxy)-6-(acetoxymethyl)tetrahydro-2H-pyran-3,4,5-triyl triacetate;
  (2S,3R,4S,5S,6R)-2-(((4aR,10aR)-7-hydroxy-1-propyl-1,2,3,4,4a,5,10,10a-octahydrobenzo [g]quinolin-6-yl) oxy)-6-(hydroxymethyl)tetrahydro-2H-pyran-3,4,5-triol;
  (2R,3R,4S,5R,6S)-2-(acetoxymethyl)-6-(((4aR,10aR)-6-hydroxy-1-propyl-1,2,3,4,4a,5,10,10a-octahydrobenzo [g]quinolin-7-yl)oxy) tetrahydro-2H-pyran-3,4,5-triyl triacetate;
  (2S,3R,4S,5R,6R)-2-(((4aR,10aR)-6-acetoxy-1-propyl-1,2,3,4,4a,5,10,10a-octahydrobenzo [g]quinolin-7-yl) oxy)-6-(acetoxymethyl)tetrahydro-2H-pyran-3,4,5-triyl triacetate;
  (2S,3R,4S,5S,6R)-2-(((4aR,10aR)-6-hydroxy-1-propyl-1,2,3,4,4a,5,10,10a-octahydrobenzo [g]quinolin-7-yl) oxy)-6-(hydroxymethyl)tetrahydro-2H-pyran-3,4,5-triol;
  [(2R,3R,4S,5R,6S)-6-[[(4aR,10aR)-1-propyl-6-[(2S,3R,4S,5R,6R)-3,4,5-triacetoxy-6-(acetoxymethyl)tetrahydropyran-2-yl]oxy-3,4,4a,5,10,10a-hexahydro-2H-benzo [g]quinolin-7-yl]oxy]-3,4,5-triacetoxy-tetrahydropyran-2-yl]methyl acetate; and
  (2R,2'R,3S,3'S,4S,4'S,5R,5'R,6S,6'S)-6,6'-(((4aR,10aR)-1-propyl-1,2,3,4,4a,5,10,10a-octahydrobenzo [g]quinoline-6,7-diyl)bis(oxy)) bis(2-(hydroxymethyl) tetrahydro-2H-pyran-3,4,5-triol);
  or a pharmaceutically acceptable salt of any of these compounds.

10. A pharmaceutical composition comprising a compound or pharmaceutically acceptable salt thereof according to claim 1, and one or more pharmaceutically acceptable excipients.

11. The pharmaceutical composition according to claim 10, wherein said pharmaceutical composition is an oral pharmaceutical composition.

12. A method for the treatment of a neurodegenerative disease or disorder, which method comprises the administration of a therapeutically effective amount of a compound or pharmaceutically acceptable salt thereof according to claim 1, to a patient in need thereof.

13. The pharmaceutical composition of claim 10, wherein the compound or pharmaceutically acceptable salt thereof is selected from the group consisting of:
  (2R,3R,4S,5R,6S)-2-(acetoxymethyl)-6-(((4aR,10aR)-7-(benzyloxy)-1-propyl-1,2,3,4,4a,5,10,10a-octahydrobenzo [g]quinolin-6-yl)oxy) tetrahydro-2H-pyran-3,4,5-triyl triacetate;
  (2R,3R,4S,5R,6S)-2-(acetoxymethyl)-6-(((4aR,10aR)-7-hydroxy-1-propyl-1,2,3,4,4a,5,10,10a-octahydrobenzo [g]quinolin-6-yl)oxy) tetrahydro-2H-pyran-3,4,5-triyl triacetate;
  (2S,3R,4S,5R,6R)-2-(((4aR,10aR)-7-acetoxy-1-propyl-1,2,3,4,4a,5,10,10a-octahydrobenzo [g]quinolin-6-yl) oxy)-6-(acetoxymethyl)tetrahydro-2H-pyran-3,4,5-triyl triacetate;
  (2S,3R,4S,5S,6R)-2-(((4aR,10aR)-7-hydroxy-1-propyl-1,2,3,4,4a,5,10,10a-octahydrobenzo [g]quinolin-6-yl) oxy)-6-(hydroxymethyl)tetrahydro-2H-pyran-3,4,5-triol;
  (2R,3R,4S,5R,6S)-2-(acetoxymethyl)-6-(((4aR,10aR)-6-hydroxy-1-propyl-1,2,3,4,4a,5,10,10a-octahydrobenzo [g]quinolin-7-yl)oxy) tetrahydro-2H-pyran-3,4,5-triyl triacetate;
  (2S,3R,4S,5R,6R)-2-(((4aR,10aR)-6-acetoxy-1-propyl-1,2,3,4,4a,5,10,10a-octahydrobenzo [g]quinolin-7-yl) oxy)-6-(acetoxymethyl)tetrahydro-2H-pyran-3,4,5-triyl triacetate;
  (2S,3R,4S,5S,6R)-2-(((4aR,10aR)-6-hydroxy-1-propyl-1,2,3,4,4a,5,10,10a-octahydrobenzo [g]quinolin-7-yl) oxy)-6-(hydroxymethyl)tetrahydro-2H-pyran-3,4,5-triol;

[(2R,3R,4S,5R,6S)-6-[[(4aR,10aR)-1-propyl-6-[(2S,3R,4S,5R,6R)-3,4,5-triacetoxy-6-(acetoxymethyl)tetrahydropyran-2-yl]oxy-3,4,4a,5,10,10a-hexahydro-2H-benzo [g]quinolin-7-yl]oxy]-3,4,5-triacetoxytetrahydropyran-2-yl]methyl acetate; and (2R,2'R,3S,3'S,4S,4'S,5R,5'R,6S,6'S)-6,6'-(((4aR,10aR)-1-propyl-1,2,3,4,4a,5,10,10a-octahydrobenzo [g]quinoline-6,7-diyl)bis(oxy)) bis(2-(hydroxymethyl)tetrahydro-2H-pyran-3,4,5-triol);

and pharmaceutically acceptable salts of these compounds.

14. The method of claim 12, wherein the compound or pharmaceutically acceptable salt thereof is selected from the group consisting of:
(2R,3R,4S,5R,6S)-2-(acetoxymethyl)-6-(((4aR,10aR)-7-(benzyloxy)-1-propyl-1,2,3,4,4a,5,10,10a-octahydrobenzo [g]quinolin-6-yl)oxy) tetrahydro-2H-pyran-3,4,5-triyl triacetate;
(2R,3R,4S,5R,6S)-2-(acetoxymethyl)-6-(((4aR,10aR)-7-hydroxy-1-propyl-1,2,3,4,4a,5,10,10a-octahydrobenzo [g]quinolin-6-yl)oxy) tetrahydro-2H-pyran-3,4,5-triyl triacetate;
(2S,3R,4S,5R,6R)-2-(((4aR,10aR)-7-acetoxy-1-propyl-1,2,3,4,4a,5,10,10a-octahydrobenzo [g]quinolin-6-yl)oxy)-6-(acetoxymethyl)tetrahydro-2H-pyran-3,4,5-triyl triacetate;
(2S,3R,4S,5S,6R)-2-(((4aR,10aR)-7-hydroxy-1-propyl-1,2,3,4,4a,5,10,10a-octahydrobenzo [g]quinolin-6-yl)oxy)-6-(hydroxymethyl)tetrahydro-2H-pyran-3,4,5-triol;
(2R,3R,4S,5R,6S)-2-(acetoxymethyl)-6-(((4aR,10aR)-6-hydroxy-1-propyl-1,2,3,4,4a,5,10,10a-octahydrobenzo [g]quinolin-7-yl)oxy) tetrahydro-2H-pyran-3,4,5-triyl triacetate;
(2S,3R,4S,5R,6R)-2-(((4aR,10aR)-6-acetoxy-1-propyl-1,2,3,4,4a,5,10,10a-octahydrobenzo [g]quinolin-7-yl)oxy)-6-(acetoxymethyl)tetrahydro-2H-pyran-3,4,5-triyl triacetate;
(2S,3R,4S,5S,6R)-2-(((4aR,10aR)-6-hydroxy-1-propyl-1,2,3,4,4a,5,10,10a-octahydrobenzo [g]quinolin-7-yl)oxy)-6-(hydroxymethyl)tetrahydro-2H-pyran-3,4,5-triol;
[(2R,3R,4S,5R,6S)-6-[[(4aR,10aR)-1-propyl-6-[(2S,3R,4S,5R,6R)-3,4,5-triacetoxy-6-(acetoxymethyl)tetrahydropyran-2-yl]oxy-3,4,4a,5,10,10a-hexahydro-2H-benzo [g]quinolin-7-yl]oxy]-3,4,5-triacetoxytetrahydropyran-2-yl]methyl acetate; and
(2R,2'R,3S,3'S,4S,4'S,5R,5'R,6S,6'S)-6,6'-(((4aR,10aR)-1-propyl-1,2,3,4,4a,5,10,10a-octahydrobenzo [g]quinoline-6,7-diyl)bis(oxy)) bis(2-(hydroxymethyl)tetrahydro-2H-pyran-3,4,5-triol);
and pharmaceutically acceptable salts of these compounds.

15. The compound or pharmaceutically acceptable salt thereof according to claim 1, wherein R1 is H; and wherein R2 is substituent (i).

16. The compound or pharmaceutically acceptable salt thereof according to claim 1, wherein R1 is substituent (i); and wherein R2 is H.

17. The compound or pharmaceutically acceptable salt thereof according to claim 2, wherein R3 is —C(O)methyl.

18. The compound or pharmaceutically acceptable salt thereof according to claim 3, wherein R3 is —C(O)methyl.

19. The compound or pharmaceutically acceptable salt thereof according to claim 4, wherein R3 is —C(O)methyl.

20. The compound according to claim 1, wherein the compound is selected from the group consisting of:
Compound (4): (2S,3R,4S,5S,6R)-2-(((4aR,10aR)-7-hydroxy-1-propyl-1,2,3,4,4a,5,10,10a-octahydrobenzo [g]quinolin-6-yl)oxy)-6-(hydroxymethyl)tetrahydro-2H-pyran-3,4,5-triol;

Compound (7): (2S,3R,4S,5S,6R)-2-(((4aR,10aR)-6-hydroxy-1-propyl-1,2,3,4,4a,5,10,10a-octahydrobenzo [g]quinolin-7-yl)oxy)-6-(hydroxymethyl)tetrahydro-2H-pyran-3,4,5-triol; and Compound (9): (2R,2'R,3S,3'S,4S,4'S,5R,5'R,6S,6'S)-6,6'-(((4aR,10aR)-1-propyl-1,2,3,4,4a,5,10,10a-octahydrobenzo [g]quinoline-6,7-diyl)bis(oxy)) bis(2-(hydroxymethyl)tetrahydro-2H-pyran-3,4,5-triol);

and pharmaceutically acceptable salts of these compounds.

21. The compound according to claim 1, wherein the compound is of the following formula:

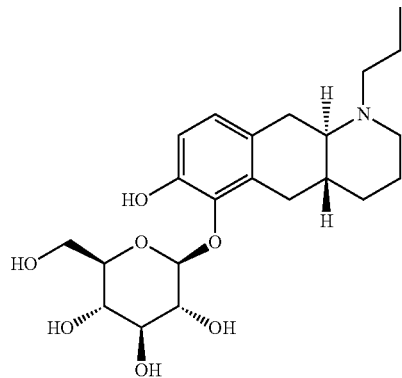 [SMILES: CCCN1CCC[C@@H]2Cc3c(ccc(O)c3O[C@@H]3O[C@H](CO)[C@@H](O)[C@H](O)[C@H]3O)C[C@H]21]

or a pharmaceutically acceptable salt thereof.

22. The compound according to claim 1, wherein the compound is of the following formula:

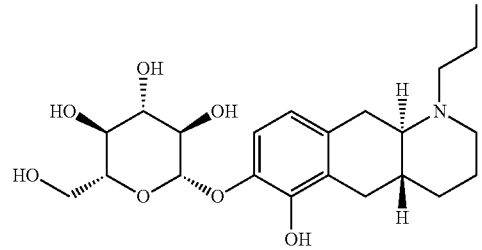 [SMILES: CCCN1CCC[C@@H]2Cc3c(ccc(O[C@@H]4O[C@H](CO)[C@@H](O)[C@H](O)[C@H]4O)c3O)C[C@H]21]

or a pharmaceutically acceptable salt thereof.

23. The compound according to claim 1, wherein the compound is of the following formula:

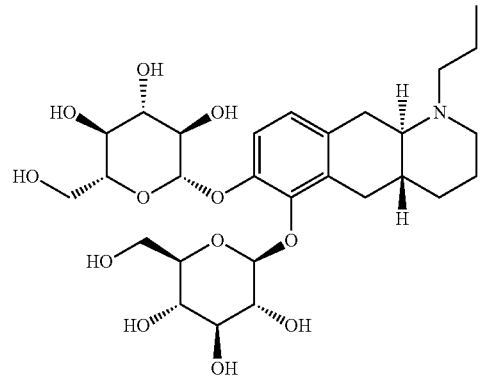 [SMILES: CCCN1CCC[C@@H]2Cc3c(ccc(O[C@@H]4O[C@H](CO)[C@@H](O)[C@H](O)[C@H]4O)c3O[C@@H]3O[C@H](CO)[C@@H](O)[C@H](O)[C@H]3O)C[C@H]21]

or a pharmaceutically acceptable salt thereof.

24. The pharmaceutical composition according to claim 10, wherein said pharmaceutical composition comprises a therapeutically effective amount of the compound or pharmaceutically acceptable salt thereof for treatment of Parkinson's Disease.

25. The pharmaceutical composition according to claim 13, wherein said pharmaceutical composition comprises a therapeutically effective amount of the compound or pharmaceutically acceptable salt thereof for treatment of Parkinson's Disease.

26. The pharmaceutical composition according to claim 13, wherein said pharmaceutical composition comprises a therapeutically effective amount of a compound selected from the group consisting of:
- Compound (4): (2S,3R,4S,5S,6R)-2-(((4aR,10aR)-7-hydroxy-1-propyl-1,2,3,4,4a,5,10, 10a-octahydrobenzo[g]quinolin-6-yl)oxy)-6-(hydroxymethyl)tetrahydro-2H-pyran-3,4,5-triol;
- Compound (7): (2S,3R,4S,5S,6R)-2-(((4aR,10aR)-6-hydroxy-1-propyl-1,2,3,4,4a,5,10, 10a-octahydrobenzo[g]quinolin-7-yl)oxy)-6-(hydroxymethyl)tetrahydro-2H-pyran-3,4,5-triol; and
- Compound (9): (2R,2'R,3S,3'S,4S,4'S,5R,5'R,6S,6'S)-6,6'-(((4aR,10aR)-1-propyl-1,2,3,4,4a,5, 10, 10a-octahydrobenzo [g]quinoline-6,7-diyl)bis(oxy)) bis(2-(hydroxymethyl)tetrahydro-2H-pyran-3,4,5-triol); and pharmaceutically acceptable salts thereof for treatment of Parkinson's Disease.

27. The method of claim 14, wherein the compound is selected from the group consisting of:
- Compound (4): (2S,3R,4S,5S,6R)-2-(((4aR,10aR)-7-hydroxy-1-propyl-1,2,3,4,4a,5,10,10a-octahydrobenzo[g]quinolin-6-yl)oxy)-6-(hydroxymethyl)tetrahydro-2H-pyran-3,4,5-triol;
- Compound (7): (2S,3R,4S,5S,6R)-2-(((4aR,10aR)-6-hydroxy-1-propyl-1,2,3,4,4a,5,10,10a-octahydrobenzo[g]quinolin-7-yl)oxy)-6-(hydroxymethyl)tetrahydro-2H-pyran-3,4,5-triol; and
- Compound (9): (2R,2'R,3S,3'S,4S,4'S,5R,5'R,6S,6'S)-6,6'-(((4aR,10aR)-1-propyl-1,2,3,4,4a,5,10,10a-octahydrobenzo [g]quinoline-6,7-diyl)bis(oxy)) bis(2-(hydroxymethyl)tetrahydro-2H-pyran-3,4,5-triol);

and pharmaceutically acceptable salts of these compounds.

28. The method of claim 14, for treatment of Parkinson's Disease.

29. The method of claim 27, for treatment of Parkinson's Disease.

* * * * *